(12) United States Patent
Somers et al.

(10) Patent No.: US 6,461,604 B1
(45) Date of Patent: Oct. 8, 2002

(54) CRYSTALLINE IL-6 AND MODELS OF THE MOLECULAR STRUCTURE OF IL-6

(75) Inventors: William S. Somers, Boston, MA (US); Mark L. Stahl, Wilmington, MA (US); Jasbir S. Seehra, Lexington, MA (US); Guang-Yi Xu, Arlington, MA (US); Thomas E. McDonagh, Acton, MA (US); Hsiang-Ai Yu, Andover, MA (US); Jin Hong, Ayer, MA (US)

(73) Assignee: Genetics Institute, LLC, Cambridge, MA (US)

( * ) Notice: Subject to any disclaimer, the term of this patent is extended or adjusted under 35 U.S.C. 154(b) by 0 days.

(21) Appl. No.: 09/499,148

(22) Filed: Feb. 7, 2000

Related U.S. Application Data

(63) Continuation of application No. 08/841,035, filed on Apr. 29, 1997, now abandoned.
(60) Provisional application No. 60/024,115, filed on Aug. 16, 1996.

(51) Int. Cl.[7] ............................. C07K 1/30; C07K 1/54; A61K 38/20
(52) U.S. Cl. ...................... 424/85.2; 530/351; 530/402; 530/412; 530/418; 530/419; 530/420; 435/69.52
(58) Field of Search ............................. 424/85.2; 514/2, 514/8, 12; 530/351, 402, 412, 419, 418, 420; 435/69.52

(56) References Cited

PUBLICATIONS

Bazan, "Haemopoietic receptors and helical cytokines," *Immunology Today*, 11:350–354 (1990).
Bazan, "Neuropoietic Cytokines in the Hematopoietic Fold," *Neuron*, 7:197–208 (Aug., 1991).
Breton et al., "Structure, stability and biological properties of a N–terminally truncated form of recombinant human interleukin–6 containing a single disulfide bond," *Eur. J. Biochem.*, 227:573–581 (1995).
deHon et al., "Functional Distinction of Two Regions of Human Interleukin 6 Important For Signal Transduction Via GP130," *Cytokine*, 7:398–407 (Jul., 1995).
Ehlers et al., "Combining Two Mutations of Human Interleukin–6 That Affect gp130 Activation Results in a Potent Interleukin–6 Receptor Antagonist on Human Myeloma Cells," *J. Biol. Chem.*, 270:8158–8163 (Apr., 1995).
Ehlers et al., "Identification of Two Novel Regions of Human IL–6 Responsible for Receptor Binding and Signal Transduction," *J. Immunology*, 153:1744–1753 (1994).
Fiorillo et al., "Analysis of human/mouse interleukin–6 hybrid proteins: both amino and carboxy termini of human interleukin–6 are required for in vitro receptor binding," *Eur. J. Immunol.*, 22:2609–2615 (1992).
Fontaine et al., "Involvement of the Arg179 in the active site of human IL–6," *Eur. J. Biochem.*, 211:749–755 (1993).
Hammacher et al., "Structure–function analysis of human IL–6: Identification of two distinct regions that are important for receptor binding," *Protein Science*, 3:2280–2293 (1994).
Hill et al., "The structure of granulocyte–colony–stimulating factor and its relationship to other growth factors," *Proc. Natl. Acad. Sci. USA*, 90:5167–5171 (Jun. 1993).
Lovejoy et al., "Crystal Structure of Canine and Bovine Granulocyte–Colony Stimulating Factor (G–CSF)," *J. Mol. Biol.*, 234:640–653 (1993).
Morton et al., "Solution structure of synthetic peptides corresponding to the C–terminal helix of interleukin–6," *Eur. J. Biochem.*, 291:97–107 (1994).
Nishimura et al., "Folding Topologies of Human Interleukin–6 and Its Mutants As Studied by NMR Spectroscopy," *Biochemistry*, 35:273–381 (1996).
Paonessa et al., "Two distinct and independent sites on IL–6 trigger gp130 dimer formation and signalling," *The EMBO Journal*, 14:1942–1951 (1995).
Somers et al., "The X–ray structure of a growth hormone–prolactin receptor complex," *Nature*, 372:478–481 (Dec. 1994).
Somers et al, "1.9 Å crystal structure of interleukin 6; implications for a novel mode of receptor dimerization and signaling," *The EMBO Journal*, 16:989–007 (1997).
Sprang et al., "Cytokine structural taxonomy and mechanisms of receptor engagement," *Curr. Opin. Struct. Bio.*, 3:815–827 (1993).
Xu et al., "Solution Structure of a Cellolose–Binding Domain from *Cellulomonas fimi* by Nuclear Magnetic Resonance Spectroscopy," *Biochemistry*, 34:6993–7009 (1995).
Xu et al., "Complete $^1$H, $^{15}$N and $^{13}$C assignments, secondary structure, and topology of recombinant human interleukin–6," *Journal of Biomolecular NMR*, 8:123–135 (1996).
Xu et al., "Solution Structure of Recombinant Human Interleukin–6," *J. Mol. Biol.*, 268:468–481 (1997).

*Primary Examiner*—Prema Mertz
(74) *Attorney, Agent, or Firm*—Rebecca Barrett Wyeth

(57) ABSTRACT

Crystallographic and NMR solution structures of human IL-6 are reported. The invention provides models and systems incorporating such structures which are useful for identifying IL-6/IL-6 receptor interactions and for identification of agonists and antagonists of such interactions. Crystalline human IL-6 is also provided.

14 Claims, 15 Drawing Sheets

(11 of 15 Drawing Sheet(s) Filed in Color)

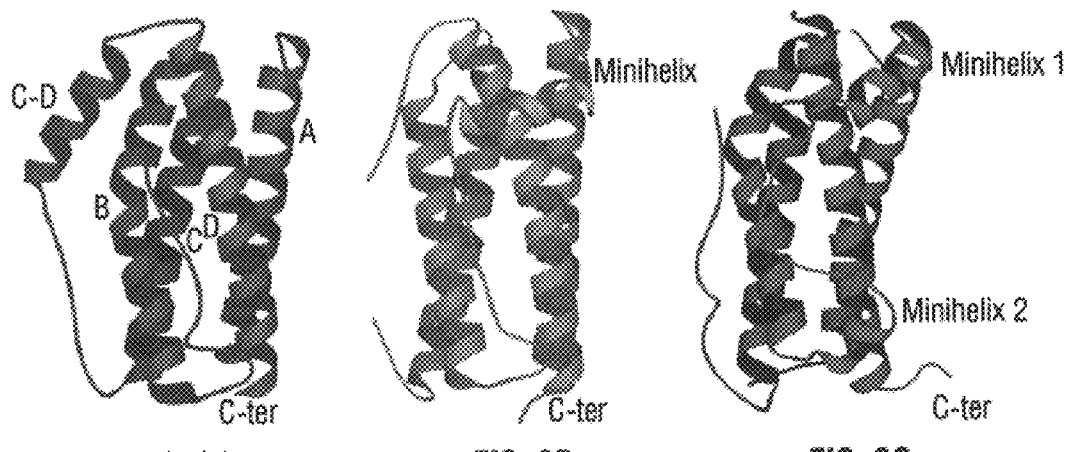
FIG. 3A  FIG. 3B  FIG. 3C
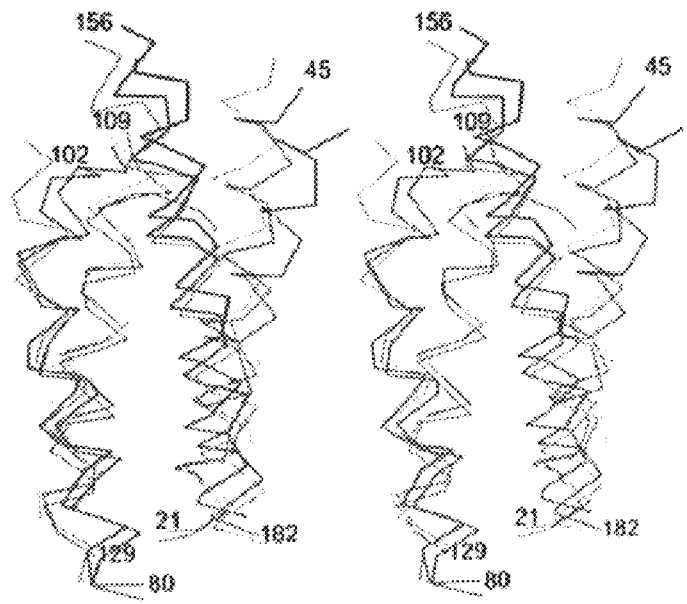
FIG. 3D

| | | | | |
|---|---|---|---|---|
| 1 averageHelixMin | LTSSERIDKQIRYILDGISALRKETCNKSNMCESSKEALAENNLNLPKM | ^AAVE:49 |
| 2 bov_il6_ed | LTTPEKTEALIKRMVDKISAMRKEICEKNDECESSKETLAENKLNLPKM | |
| 3 cat_il6_ed | LTSADKMEELIKYILGKISALKKEMCDNYNKCEDSKEALAEMNLNLPKL | |
| 4 rhesus_il6_ed | LTSSERIDKHIRYILDGISALRKETCNRSNMCESSKEALAENNLNLPKM | |
| 5 sheep_il6_ed | LTTPEKTEALIKHIVDKISAIRKEICEKNDECENSKETLAENKLKLPKM | |
| 6 rat_il6_ed | YTTSQ_VGGLITYVLREILEMRKELCNGNSDCMNSDDALSENNLKLPEI | |
| 7 mouse_il6_ed | YTTSQ_VGGLITHVLWEIVEMRKELCNGNSDCMNNDDALAENNLNLPKL | |
| 8 seaotter_il6_ed | LTSADKMEDFIKFILGKISALRNEMCDKYNKCEDSKEVLAENNLNLPKL | |
| 9 pig_il6_ed | FTSPDKTEELIKYILGKISAMRKEMCEKYEKCENSKEVLAENNLNLPKM | |
| Consensus | T     I      H          I        E C       C        L EN L LP | |

^AAVE:29    ^AAVE:39    ^AAVE:49    ^AAVE:59

| | | |
|---|---|---|
| 1 averageHelixMin | AEKDGCFQSGFNEETCLVKIITGLLEFEVYLEYLQNRFESSE_EQARAVQ | ^AAVE:109 |
| 2 bov_il6_ed | EEKDGCFQSGFNQAICLIRTTAGLLEYQIYLDYLQNEYEGNQ_ENVRDLR | |
| 3 cat_il6_ed | AEKDGCFQSGFNQETCLTRTTGLQEFQIYLKFLQDKYEGDE_ENAKSVY | |
| 4 rhesus_il6_ed | AEKDGCFQSGFNEDTCLVKIITGLLEFEVYLEYLQNRFESSE_EQARAVQ | |
| 5 sheep_il6_ed | EEKDGCFQSGFNQAICLIKTTAGLLEYQIYLDFLQNEFEGNQ_ETVMELQ | |
| 6 rat_il6_ed | QRNDGCFQTGYNQEICLLKICSGLLEFRFYLEFVKNNLQDNKKDKARVIQ | |
| 7 mouse_il6_ed | QRNDGCYQTGYNQEICLLKISSGLLEYHSYLEYMKNNLKDNKKDKARVLQ | |
| 8 seaotter_il6_ed | AEKDRCEQSRFNQETCLTRTTGLQEFQIHLKYLESNYEGNK_DNAHSVY | |
| 9 pig_il6_ed | AEKDGCFQSGFNQETCLMRITTGLVEFQIYLDYLQKEYESNK_GNVEAVQ | |
| Consensus | D CQ  N  CL            GL E      L | |

^AAVE:69    ^AAVE:79    ^AAVE:89    ^AAVE:99    ^AAVE:109

*FIG. 12A*

```
1 averageHelixMin  MSTKVLIQFLQKKAKNLDAITTPDPTTNASLLTKLQAQNQWLQDMTTHLI
2 bov_il6_ed        KNIRTLIQILKQK   IADLITTP   ATNTDLLEKMQSSNEWVKNAKIILI
3 cat_il6_ed        TSTNVLLQMLKRRGKNQDEVTIPVPTVEVGLQAKLQSQEEWLRHTTIHLT
4 rhesus_il6_ed     MSTKVLIQFLQKKAKNLDAITTPEPTTNASLLTKLQAQNQWLQDMTTHLI
5 sheep_il6_ed      SSIRTLIQILKEK   IAGLITTP   ATHTDMLEKMQSSNEWVKNAKVII
6 rat_il6_ed        SNTETLVHIFKQEIKDSYKIVLPTPTSNALLMEKLESQKEWLRTKTIQLI
7 mouse_il6_ed      RDTETLIHIFNQEVKDLHKIVLPTPISNALLTDKLESQKEWLRTKTIQFI
8 seaotter_il6_ed   ISTKHLLQTLRPM   NQIEVTTPDPTTDASLQALFKSQDKWLKHTTIHLI
9 pig_il6_ed        ISTKALIQTLRQKGKNPDKATTPNPTTNAGLLDKLQSQNEWMKNTKILLI
  Consensus                       L                                  W
                 ^AAVE:118 ^AAVE:128 ^AAVE:138 ^AAVE:148 ^AAVE:158

1 averageHelixMin  LRSFKEFLQSSLRALRQM
2 bov_il6_ed       LRNLENFLQFSLRAIRMK
3 cat_il6_ed       LRRLEDFLQFSLRAVRIM
4 rhesus_il6_ed    LRSFKEFLQSNLRALRQM
5 sheep_il6_ed     LRSLENFLQFSLRAIRMK
6 rat_il6_ed       LKALEEFLKVTMRSTRQT
7 mouse_il6_ed     LKSLEEFLKVTLRSTRQT
8 seaotter_il6_ed  LRRLEDFLQFSLRAIRIM
9 pig_il6_ed       LRSLEDFLQFSLRAIRIM
  Consensus       L   FL   R  R
                 ^AAVE:168 ^AAVE:178
```

FIG. 12B

CRYSTALLINE IL-6 AND MODELS OF THE MOLECULAR STRUCTURE OF IL-6

This application claims priority from provisional application Ser. No. 60/024,115, filed Aug. 16, 1996. It is a continuation of application Ser. No. 08/841,035 filed Apr. 29, 1997 entilted "Crystalline IL-6 and Models of the Molecular Structure of IL-6," now abandoned.

BACKGROUND OF THE INVENTION

IL-6 is a pleiotropic cytokine with a variety of stimulatory effects on hematopoietic cells and cells of the immune system (Hirano et al., 1986; Wong et al., 1988; Kishimoto et al., 1992). Major cellular targets include B-lymphocytes, T-lymphocytes, the enhancement of hematopoietic colony formation and the production of acute phase response proteins in the liver (Mackiewicz et al., 1992). The primary role of IL-6 appears to be as a component of the immune system, with knock out mice exhibiting an impaired IgG and IgA response. Of particular interest is the observation of the involvement of IL-6 in bone homeostasis. In Paget's disease and in multiple myeloma patients where significant bone loss occurs, a good correlation has been found with increased IL-6 levels. Interestingly, the level of IL-6 is affected by estrogen in bone marrow derived stromal cells and causes decrease in the development of osteoclasts (Girasole et al., 1992), while estrogen loss (by mouse ovariectomy) causes enhanced osteoclast development in ex vivo cultures of bone marrow and increased osteoclasts in trabecular bone. Most importantly osteoclast development was inhibited by the in vivo or in vitro administration of estrogen or neutralizing IL-6 monoclonal antibodies (Jilka et al., 1992). Mutant mice lacking IL-6 have normal amounts of trabecular bone and, ovariectomy does not cause bone loss or a change in the rate of remodeling. These studies strongly suggest that IL-6 plays an important role in post menopausal bone loss.

Interleukin-6 (IL-6) is a member of a family of cytokines/growth factors which are believed to share a common topological fold despite limited amino acid sequence homology. All of these cytokines are believed to have three dimensional structures comprised of a core bundle of 4 $\alpha$-helices connected by variable-lengthloops. Together with, inter alia, IL-11, IL-12, and EPO, IL-6 has been classified into a subfamily of "long chain" 4-helix bundles which share several structural features including overall polypeptide chain length, average length of helices, and characteristic packing of the antiparallel helical pairs (Sprang and Bazan, 1993). These predicted structural features for long chain 4-helix bundles have been largely confirmed by recent NMR and X-ray crystallographic studies of growth hormone, G-CSF, LIF, and CNTF (Zink et al., 1994; Hill et al., 1993; McDonald et al., 1995; Robinson et al., 1994; Ultsch et al., 1994). However, comparable experimental data on IL-6 has yet to be reported, although the sequence-specific assignments, secondary structure analysis, and overall topological fold for IL-6 have been reported (Xu et al., 1996).

The members of this cytokine family including IL-6 also share remarkably similar structural features for the receptors to which they bind. These similarities also extend to the sequential clustering events leading to transduction. The closest members of the family include LIF, CNTF, Oncostatin M, and IL-11 (Kishimoto et al., 1992; Miyajima et al., 1992; Gearing et al., 1991; Davis et al., 1991; Yamasaki et al., 1988; Kishimoto et al., 1994). The IL-6 receptor consists of two polypeptides: the $\alpha$ chain (IL-6r), an 80 kD transmembrane glycoprotein that binds IL-6 with low affinity, and the $\beta$ chain (gp130), a 130 kD transmembrane glycoprotein that binds to the IL-6/IL-6r heterodimer to form the high affinity signal transducing complex (Taga et al., 1989). gp130 is a signal transducticn component of not only the IL-6 receptor but also the LIF, CNTF, Oncostatin M, and the IL-11 receptors (Taga et al., 1992), therefore the $\alpha$ chain distribution dictates the cellular response (Kishimoto et al., 1992). The IL-6r is a transmembrane protein composed of a cytokine binding type I domain (necessary and sufficient for binding IL-6) (Yawata et al., 1993), an Ig like domain and a short cytosolic domain (Yamasaki et al., 1988) that is not required for signalling (Taga et al., 1989). gp130 is also a transmembrane protein composed of an Ig-like domain, cytokine type I domain, a contacting-like region, a transmembrane domain, and a cytosolic domain necessary for signalling, containing a motif known as box 1, box2 (Murakami et al., 1991). Signal transduction by IL-6 follows the dimerisation of gp130, which activates a bound JAK2 (Argetsinger et al., 1993).

Recently studies utilising size exclusion columns and equilibrium centrifugation have shown that IL-6 binds to sIL-6r to form a heterodimer (Ward et al., 1994). However, in the presence of sgp130 a hexameric complex is formed that is composed of IL-6, sIL-6r, sgp130 in a 2:2:2 stoichiometry (Ward et al., 1994). These studies combined with the evidence from structural, biochemical, and mutagenesis studies of the human growth hormone (hGH), human growth hormone receptor (hGHr), human prolactin receptor (hPRLr) complexes (De Vos et al., 1992; Somers et al., 1994) provide evidence that assembly of the IL-6 signalling complex is an ordered and sequential process.

Analysis of IL-6 site-directed mutagenesis data provides further support for such a structural model The first class of IL-6 mutants (site 1) show reduced binding to IL-6r (Savino et al., 1993). Two additional, distinct classes of IL-6 mutants (sites 2 and 3) have been isolated which bind to IL-6r and yet fail to transduce (Brakenhoff et al., 1994; Ehlers et al., 1994). IL-6 with both site 2 and site 3 mutations not only fails to transduce signal but functions as an antagonist in an IL-6 dependant proliferation assay (Brakenhoff et al., 1994). IL-6r point mutants have also been identified which result in normal IL-6 binding but no signal transduction (Yawata et al., 1993). It has been speculated that these mutations are in a region of IL-6r that is involved in low affinity binding to gp130.

However, the study of IL-6 and its interaction with its receptor components has been hindered by the lack of detailed information concerning the structure of IL-6. Therefore, it would be desirable to determine the structure of IL-6 in order to better enable the study of its interactions with its receptor and to identify possible inhibitors of the IL-6/IL-6r interaction.

SUMMARY OF THE INVENTION

The present invention provides for the first time crystalline IL-6. Preferably, the crystalline IL-6 human IL-6; however, crystalline IL-6 from non-mammalian species is also encompasssed by the invention. The crystalline IL-6 may be recombinant IL-6 or IL-6 purified from naturally occurring or other non-recombinant sources; however, crystalline recombinant IL-6 is preferred. In certain preferred embodiments,the IL-6 may be glycosylated, although non-glycosylated forms are also contemplated by the present invention. In other embodiments, the crystalline IL-6 may comprise the mature sequence of naturally-occurring IL-6, although other forms (such as, for example, IL-6 comprising an additional N-terminal methionine residue) are also encompassed by the invention.

The present invention also provides for crystallization of IL-6 in association with a second chemical species, including without limitation potential inhibitors of IL-6 activity, potential inhibitors of IL-6 binding and all or a portion of the IL-6 receptor (IL-6R).

Other aspects of the invention provide for a model of the structure of IL-6 comprising a data set embodying the structure of IL-6. The data set embodying such structure can be derived from any available means for obtaining such information, including without limitation by crystallographicanalysis of IL-6 and by NMR analysis of IL-6. Such model can embody the entire structure of IL-6 or a portion of such structure. Preferably, the portion of the IL-6 structure embodied by such model comprises the active binding site of IL-6 and/or another epitope or binding domain of IL-6.

Any available method may be used to construct such model from the crystallographic and/or NMR data disclosed herein or obtained from independent analysis of crystalline IL-6. Such a model can be constructed from available analytical data points using known software packages such as HKL, MOSFILM, XDS, CCP4, SHARP, PHASES, HEAVY, XPLOR, TNT, NMRCOMPASS, NMRPIPE, DIANA, NMRDRAW, FELIX, VNMR, MADIGRAS, QUANTA, O, FRODO, RASMOL, and CHAIN. The model constructed from these data can then be visualized using available systems, including, for example, Silicon Graphics, Evans and Sutherland, SUN, Hewlett Packard, Apple Macintosh, DEC, IBM, and Compaq. The present invention also provides for a computer system which comprises the model of the invention and hardware used for construction, processing and/or visualization of the model of the invention.

The model of the present invention is particularly useful in methods of identifying a species which is an agonist or antagonist of IL-6 activity or binding comprising: (a) providing the model of the invention, (b) studying the interaction of candidate species with such model, and (c) selecting a species which is predicted to act as said agonist or antagonist. The model of the invention is also useful in: (a) a process of identifying a substance that inhibits IL-6 activity or binding comprising determining the interaction between a candidate substance and a model of the structure of IL-6; and (b) a process of identifying a substance that mimics IL-6 activity or binding comprising determining the interaction between a candidate substance and a model of the structure of IL-6. The study of the interaction of the candidate species with the model can be performed using available software platforms, including QUANTA, RASMOL, O, CHAIN, FRODO, INSIGHT, DOCK, MCSS/HOOK, CHARMM, LEAPFROG, CAVEAT(UC Berkley), CAVEAT(MSI), MODELLER, CATALYST, and ISIS.

DESCRIPTION OF THE FIGURES

The patent or application file contains at least one drawing executed in color. Copies of this patent or patent application publication with color drawing(s) will be provided by the Office upon request and payment of the necessary fee.

FIG. 3: A comparison of the crystal structures of IL-6 (FIG. 3A), hG-CSF (FIG. 3B), and hGH (FIG. 3C). The C-termini are labeled along with main helices and extra helices in the loops. FIG. 3D is a stereo Cα trace of IL-6 (red) main four helices superimposed on the corresponding sections of hG-CSF (green) and hGH (blue). The figure was produced with MOLSCRIPT (Kraulis, 1991 #121).

FIG. 12A & FIG. 2B: Multiple sequence alignment for IL-6 from nine mammalian species.

DETAILED DESCRIPTION OF PREFERRED EMBODIMENTS

Crystallization of Human Recombinant IL-6 and Determination of Crystallographic Structure We report here the 1.9 Å X-ray structure of human recombinant IL-6 and compare the structure of IL-6 to known structures of other closely related cytokines. The availability of the three dimensional structure allows a detailed interpretation of previously reported mutagenesis studies and a better understanding of how they affect IL-6r/gp130 binding. A three dimensional model of the hexameric IL-6 receptor complex is also presented based upon reported mutagenesis studies, biochemical data, and the structure of the hGH receptor complex. Based on our model, we predict a fourth binding site on IL-6, a IL-6/IL-6 interaction, which may be necessary for the sequential assembly of a functional hexameric IL-6 receptor complex.

Protein Structure

Figure 1:
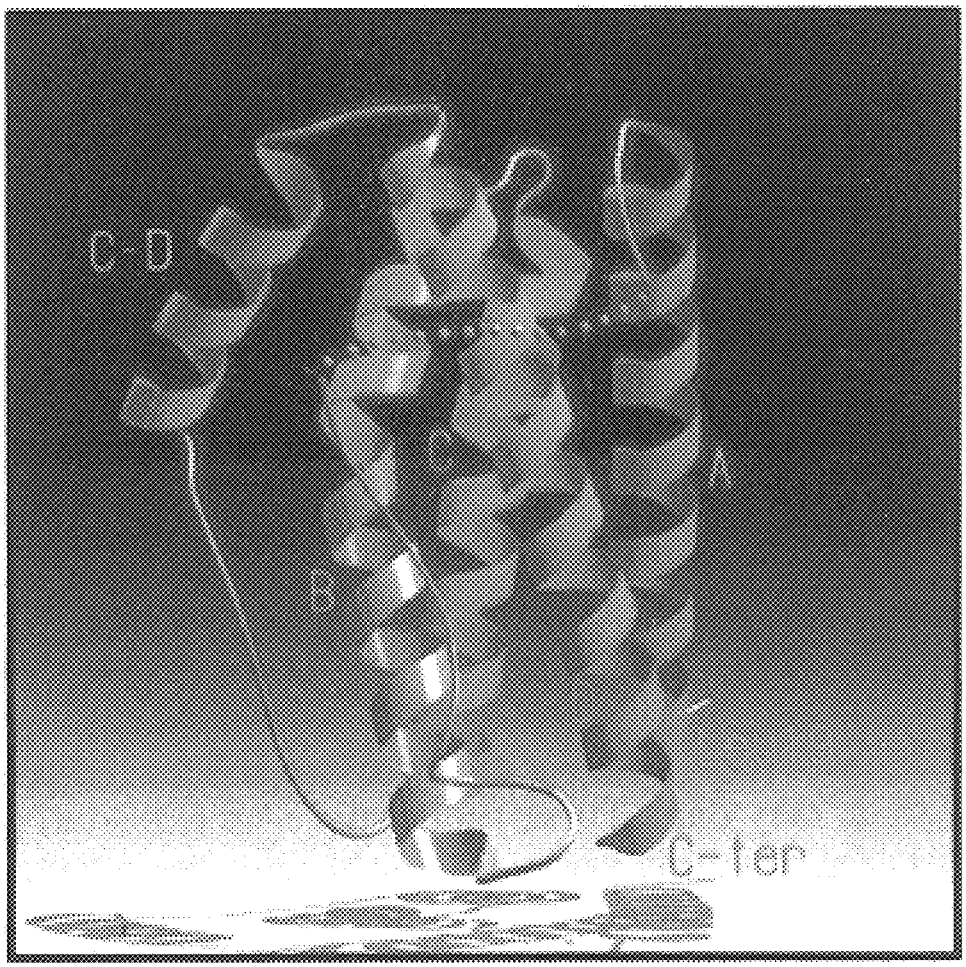
FIG. 1: Ribbon representation of the IL-6 crystal structure. The four main helices are labeled A, B, C, and D. The extra helix in the final long loop is labeled C-D. The missing part of the first cross-over connection is indicated by a dashed line. The figure was created using RAYSCRIPT, a modified version of MOLSCRIPT (Kraulis, 1991 #121).

The crystal structure of IL-6 (FIG. 1) is a four helix bundle with a topology that has now been seen for a number of other cytokines in the superfamily described by Bazan (Bazan, 1990; Bazan, 1991; Sprang and Bazan, 1993). The four helices are arranged so that the helices A and B run in the same direction and C and D in the opposite. Linking the helices in this arrangement is made possible by a long loop joining the A and B helices, a short one between B and C and finally a second long connection between C and the fourth main helix D.

Backbone Structure

The N-terminal 18 amino acids of IL-6 are not visible in electron density maps and consequently have not been modeled. The first long helix (A) extends from Ser21 to Asn45 and is connected to helix B by a 25 amino acid loop. The first structural feature of the inter-helix connection is a loop formed by a disulphide bond between cysteines 44 and 50. Cys50 is poorly ordered and precedes an 8 residue break with no interpretable electron density. This break is followed by Asn61 to Glu69 in an extended conformations which presents the hydrophobic side chains of Leu62, Leu64, Pro65 and Met67 into a cleft between helices B and D. Before the start of helix B, the final section of the loop is defined by three structural elements, a type I β turn (Ala68-Asp71), a disulphide (Cys73-Cys83) and a type II β turn (Gln75-Phe78).

Helix B (Glu80 to Gln102) has average $\phi,\psi$ torsion angles of $-63.8°$ and $-39.5°$. The $\phi,\psi$ values for Glu93 and Phe94 are $-64.5°,-25.6°$ and $-76.8°,-16.5°$ respectively, caused by a 38° bend in the direction of the helix axis centered at these residues. This bend results in a break in the α-helical hydrogen bonding pattern, such that Leu92 O is hydrogen bonded to Val 96 N via water 19. The short cross-over connection between helices B and C extends from Asn 103 to Ser 108 and has higher than average B factors (37.9 $Å^2$).

Helix C (Glu109-Lys129) is followed by the second long crossover connection. Residues Leu133 to Asp140 are in an extended conformation interacting with helix B via the hydrophobic side chains of Leu133, Ile136, and Pro139. Following this there is an additional short helix lying outside the main four helical bundle. The three turns of this helix are formed by amino acids from Pro141 to Gln152.

Residues Gln156 to Arg182 form the final D helix. Located at the N-terminus of this helix is the only tryptophan (157) in IL-6. In solution this tryptophan would be solvent exposed but in the crystal is buried in a hydrophobic pocket made by two symmetry related molecules. The two C-terminal residues of IL-6, Gln183 and Met184, have higher than average B-factors (35.8 Å2) but good electron density.

Side Chain Contacts

The relative disposition of the four main helices of IL-6 is maintained by a network of hydrophobic interactions in the core of the molecule. These interactions occur in layers of residues down the entire axis of the bundle. The lower end of the core (FIG. 1) is capped by a hydrogen bond between the side chains of Lys129 and Ser22 and hydrophobic interactions between Leu84 and Met184. The core residues are Ile25, Ile29, Ile32, Ile36, Leu39, Thr43, Ile87, Leu91, Leu98, Leu101, Phe105, Ala112, Val115, Thr119, Leu122, Leu126, Thr163, Leu167, Phe170, Leu174, Ser177 and Leu181. This core is terminated at the other end by a hydrogen bond between Ser108 and Glu42. Side chains in the core that are capable of forming hydrogen bonds, make interactions away from the center. Thr43 $O_\gamma$ interacts with an ordered water, Thr119 $O_\gamma$ donates a hydrogen bond to Val115 O, Thr163 $O_\gamma$ donates a hydrogen bond to Gln159 O and Ser177 $O_\gamma$ donates to Phe173 O. On the outside of this main hydrophobic core lies a cluster of hydrophobic side chains stabilising the position of the C-D mini-helix. This mini-helix presents the side chains of three Leucines (147, 148,151) towards the hydrophobic side chains of helix B (Val96, Tyr97, Tyr100), helix D (Thr162) and the A-B loop (Leu62).

In contrast to the large number of hydrophobic interactions stabilising the fold of IL-6, only three hydrogen bonds bridge the main helices. Indeed, helix A has no hydrogen bonds with the other helices. Helices B and C interact via a hydrogen bond between the O$\epsilon$1 of Glu95 and N$\zeta$ of Lys120 (2.5 Å). The only other two hydrogen bonds between helices B and D are formed by, Arg104 N$\eta$2 to Asp160O$\delta$1 (3.0 Å) and Tyr100 O$\eta$ to Gln159 N$\epsilon$2 (2.8 Å). In addition, there is a considerable network of indirect hydrogen bonds via networks of ordered water molecules (described below).

The crystal structure of IL-6 shows that the side chains of Asp26, Arg30 and Met117 each exist in two discrete conformations. The Asp and Arg residues interact with each other and are next to a crystallographic two-fold axis. In one state Arg30 donates a hydrogen bond (2.8 Å) from the N$\epsilon$ to O$\delta$1 of Asp26 ($\chi$1=-174°). In the second state, rotation of $\chi$ torsion angles (Asp26 $\chi$1=-73°) breaks this hydrogen bond so the arginine now donates a hydrogen bond to water34 (2.8 Å) and Asp26 hydrogen bonds to water55 (2.6 Å). In the first conformation, Arg30 interacts with itself and makes a close contact to Asp26 (1.7 Å) through the crystallographic two-fold axis so that adjacent molecules require the second conformation.

Trp157 which lies at the N-terminal end of helix D is almost completely solvent exposed aside from contacts (3.5 Å) with the C$\epsilon$ of Met49. Despite being solvent exposed, this tryptophan is highly ordered through its interactions with a symmetry related molecule and penetrates deep into a hydrophobic pocket created by the side chains of helices A (Tyr31 and Gly35) and C (Ala114, Val115 and Ser118). The solvent accessibility of the tryptophan is consistant with the fluorescence emission spectra with $\epsilon_{s_{max}} \sim 336$ nm (data not shown).

Ordered Water

The current model of IL-6 contains 121 ordered water molecules, of which 105 have temperature factors ranging from 15.4 $Å^2$ to 50.0 $Å^2$ (16 water molecules have temperature factors above 50.0 $Å^2$). There are only two water molecules in the second shell which do not directly interact with protein. The ordered water molecules are not distributed uniformly over the entire surface of IL-6 but are localised to clefts in the surface. These water molecules form networks of hydrogen bonds that link the helices and loops that stabilise the crystal structure. One water molecule (47) is completely buried between helices B and C and bridges the two helices by forming hydrogen bonds to the carbonyl oxygens of Ala112 (2.8 Å) and Leu98 (3.0 Å).

Figure 2:
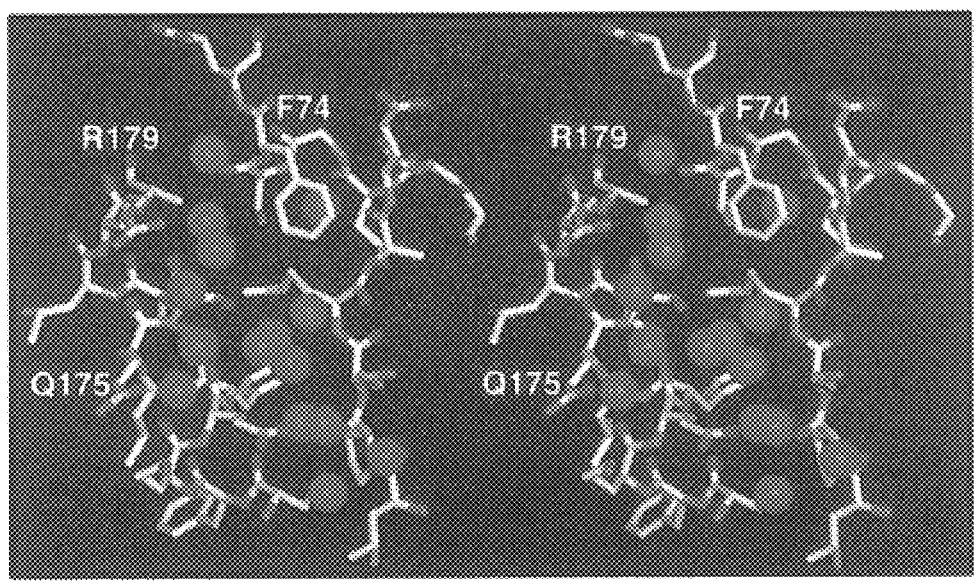
FIG. 2: Stereo view of the water structure in the region between the D helix and the A-B loop of IL-6. The water molecules are shown as red spheres and the protein as a stick representation.

The highest density of water is found in the region between the C-terminal regions of helix D and the A-B loop (FIG. 2). There are 18 water molecules and two sulphates in this region that form a network of hydrogen bonds linking these two secondary structural elements. From modeling studies described later, this region may be involved in binding to the IL-6r.

Small Molecule Binding

The crystal structure of IL-6 has a single L(+)-tartaric acid molecule bound on a crystallographic two fold axis giving a stoichiometry of one tartrate bound to two molecules of IL-6. The binding is mediated by direct hydrogen bonds from Arg182 NE (2.8 Å) and NH2 (2.7 Å) to one carboxyl group of tartrate. The same carboxyl atoms hydrogen bond with Arg179 NE (2.8 Å) and water6 (3.0 Å). In addition the α-OH of tartrate accepts a hydrogen bond from Arg179 NH2 (3.0 Å) and the β-OH donates a hydrogen bond to the O of Gln175 (2.8 Å). Since the tartrate lies on a crystallographic two fold axis, these interactions are duplicated on the other half of the tartrate from a symmetry related molecule satisfying almost every possible hydrogen bond.

Structural comparison of IL-6 with G-CSF and hGH

The four helix bundle up-up, down-down topology of the helices seen in the structure of IL-6 was predicted by Bazan (Bazan, 1990; Bazan, 1991; Sprang and Bazan, 1993) to be a common structural fold for cytokines. Although the members of the superfamily share low homology at the amino acid level, the 3 dimensional structures of several cytokines reveal a remarkable similarity. G-CSF, with 16% amino acid sequence identity, is the closest member of the superfamily for which a three dimensional structure is available (Bazan, 1991). The structures of human G-CSF (Hill et al., 1993), canine G-CSF and bovine G-CSF (Lovejoy et al., 1993) have all been determined to high resolution. Human G-CSF, with the most ordered residues, has been chosen for a detailed comparison with IL-6. hGH shares only 9% amino acid sequence identity with IL-6. hGH has been examined crystallographically in complex with its receptor (De Vos et al., 1992) so that a comparison with IL-6 gives insights into the interaction of IL-6 with its receptor and gp130.

The superposition of G-CSF (FIG. 3D) on IL-6 using 88 Cα atoms in the helices gives an agreement of 1.1 Å RMS between the two structures. For the more distantly related hGH, the agreement is only 1.4 Å RMS over 83 atoms. This superposition reveals a good agreement in both the inter-helix angles and length of helices in these cytokines. However, a close examination reveals significant differences in several regions. The N-termini of IL-6 and G-CSF are disordered so that the crystal structures of both begin at the start of helix A, whereas the amino terminal residues of hGH are ordered and are involved in receptor binding. Helix A is the same length for all three cytokines but do not superimpose well at the C-terminal end. The largest differences at the C-terminal end of this helix are seen for hGH which may be influenced by the position of the short loop between helices B and C. Following helix A, the first long loop exhibits considerable conformational variability. The disulphide bonds in G-CSF and IL-6 in this region stabilise a very similar conformation for the A-B loop immediately after helix A. However, immediately following this, IL-6 is disordered while the other cytokines have short helical segments. The final part of the loop has the second conserved disulphide which contains IL-6 and G-CSF to adopt very similar conformations whereas hGH has a second short helix (FIGS. 3A, 3B & 3C, respectively).

Helix B superimposes well at the N-terminus for all three cytokines. IL-6 and hGH both have kinks in the same position in helix B due to a break in the hydrogen bonding and continue to superimpose well after this point. G-CSF does not have this break and extends for another turn. The short loop that connects helices B and C has a different conformation in each case while hGH includes a three residue insertion, which allows the loop to extend much closer to helix A.

Helix C superimposes well for all three cytokines except in hGH, where it is four residues shorter at the amino terminus. The long loop following helix C is well ordered in IL-6 but lacks residues present in the other two cytokines. At the end of this loop, IL-6 has a helical segment while G-CSF has a short segment of extended conformation. The final long helix (D) is the same length for each structure but does not superimpose well for hGH, which has 10 additional residues extending beyond the C-termini of the other two cytokines.

Discussion

IL-6 is a member of the four helix bundle cytokine superfamily which share structural similarities and may share common modes of receptor engagement and activation. These similarities enable signalling models to be constructed that account for the available mutagenesis data. The crystal structure of hGH bound to two molecules of hGHr (De Vos et al., 1992) has provided a useful model for the activation of cytokine receptors upon ligand binding. hGH initially binds an hGHr via a high affinity site on the surface of the cytokine. This dimer of one hGH and one hGHr then binds to a second hGHr. The binding site for the second hGHr is made up of a combination of two low affinity sites: one on the surface of hGH and a site in the C-terminal domain of the first bound receptor. This combination of high and low affinity sites on the surface of hGH ensures that the clustering of hGHr molecules, leading to signalling, is an ordered event.

Figure 4:
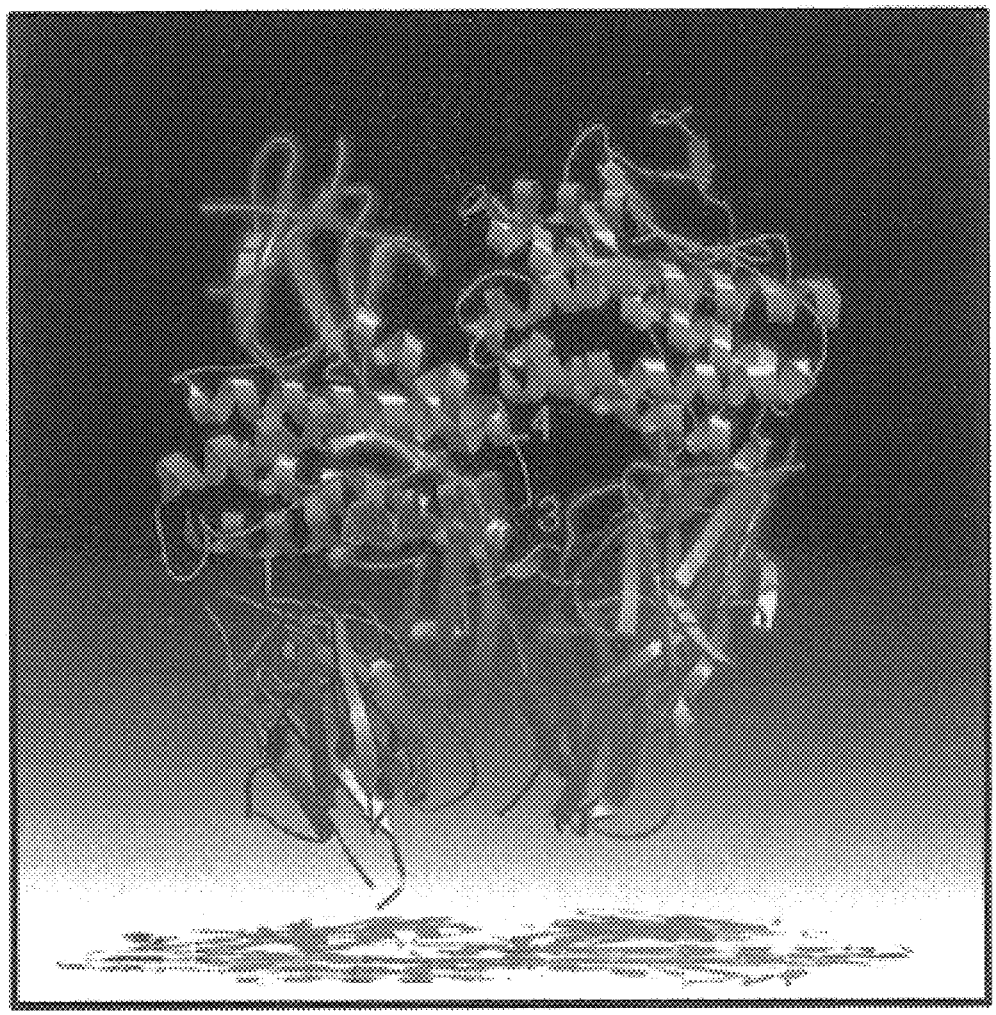
FIG. 4: A ribbon representation of the IL-6, IL-6r, gp130 hexamer signaling model. The IL-6 crystal structure is shown in green, IL-6r in blue, and gp130 in red. The proposed binding sites are labeled. Site 1 is the site of IL-6 to IL-6r interactions. Site 2 is the region where IL-6 interacts with gp130 in the trimmer. Site 3 is the site of IL-6 to gp130 interactions between trimers. Site 4 is the location of IL-6 to IL-6 interactions between trimers.

IL-6 mediated signal transduction has been shown to occur through clustering of two gp130 receptors by IL-6 (Murakami et al., 1993) or an agonistic anti-gp130 monoclonal antibody (Wijdenes et al., 1995). IL-6 binds to a single molecule of IL-6r and forms a heterodimer. In an analogous manner to hGH signalling, this heterodimer is capable of binding to gp130 to form a heterotrimer (IL-6, IL-6r, and gp130) with 1:1:1 stoichiometry. Since signalling has been demonstrated to occur through clustering of gp130 molecules, an additional binding step is necessary. Indeed, ultracentrifugation experiments with soluble IL-6, IL-6r and gp130 give a hexamer composed of two molecules of each component (Ward et al., 1994), providing support for an additional clustering event Recently, Paonessa and co-workers (Paonessa et al., 1995) presented a model of such a hexamer which was based on a model of IL-6, the hGH receptor complex (De Vos et al., 1992), and information from biochemical studies. We present a more detailed model of the signalling complex based on the high resolution structure of IL-6 in FIG. 4. This model can be used to rationalise the mutagenesis studies of IL-6.

The first event in signal transduction is the binding of soluble IL-6 through site 1 to IL-6r, forming a heterodimer. The second event is the binding of this heterodimer to gp130 on the cell surface. This binding event is mediated through site 2 on IL-6 interacting with gp-130 as well as contacts between the C-terminal domains of IL-6r and gp130. The third event to take place in IL-6 signalling is the binding of two hetero-trimeric complexes mediated by interactions in sites 3 (IL-6$_{trimer\,1}$-gp130$_{trimer\,2}$) and 4 (IL-6$_{trimer\,1}$-IL-6$_{trimer\,2}$). This model predicts the possibility of additional interactions between different trimers via the C-terminal halves of the cytokine binding domains of IL-6r and gp130.

Numerous mutagenesis studies have been performed on IL-6 in an effort to define the receptor binding sites (Fontaine et al., 1993; Savino et al., 1993; Ehlers et al., 1994; Savino et al., 1994b; de Hon et al., 1995; Ehlers et al., 1995; Fiorillo et al., 1992; Hammacher et al., 1994). The data from these mutagenesis studies are re-examined in light of the high resolution crystal structure of IL-6.

Figure 5:
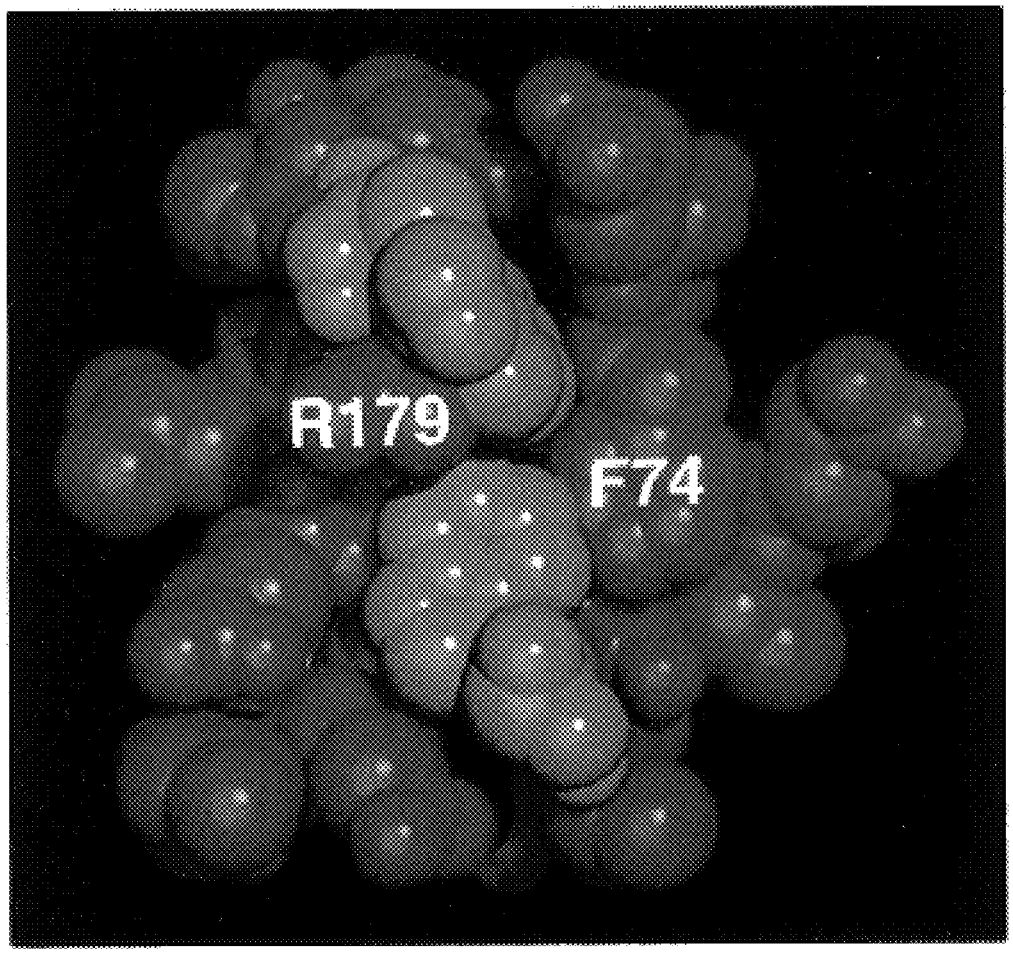
FIG. 5: A Van der Waals representation of site 1 on IL-6 (magenta), proposed to be the location of the IL-6r binding. In blue are tryptophans 104 and 169 from hGHr positioned by superimposing IL-6 on hGH in the hGHr complex (De Vos, 1992 #3). The residues labeled on IL-6 are found to be binding determinants by mutagenesis.

Site 1 mutants discussed by Savino and co-workers (Savino et al., 1993) are consistent with the hexamer model and map to a region on hGH found to be essential for hGHr binding (Cunningham and Wells, 1989). The two most important binding determinants on hGHr for hGH were found to be tryptophans 104 and 169 (Clackson and Wells, 1995). These tryptophans are inserted into pockets created by mutationally sensitive hGH residues. After superimposition of IL-6 onto hGH in the receptor complex it is found that these tryptophans from hGHr are inserted into a cleft on the surface of IL-6. A sequence alignment of receptors shows that IL-6r does not have equivalent tryptophans but may use other large or aromatic residues to bind to the surface of IL-6. The importance of this cleft in the surface of IL-6 is demonstrated by the fact that mutants that affect binding of IL-6r all map to this region (FIG. 5). Consistent with this model a 100-fold decrease in activity is observed upon mutation of Arg179 to Ala (Fontaine et al., 1993). Mutation of Gln175 to Ala results in a 5-fold decrease in activity (Savino et al., 1993). Interestingly, replacement of Ser176 with Arg causes a 4-fold increase in the activity of IL-6 (Savino et al., 1993). The equivalent residue in hGH is Lys172 and forms the pocket that accepts the tryptophan from hGHr. Arg182 (Lutticken et al., 1991) and Phe74 also form the sides of the cleft and are mutationally sensitive. Other mutations in this region which affect binding, Ser177, Ala180, Leu178, and Leu181 are all buried and may be affecting activity by altering the local conformation of IL-6.

Site 2 mutations, which bind normally to IL-6 but have reduced affinity for binding to the first molecule of gp130 (Savino et al., 1994b; Savino et al., 1994a) are also consistent with the hexamer model. These mutations are localised to a region on helices A and C and consist of Tyr31 to Asp, Gly35 to Phe, Ser118 to Arg, and Val121 to Asp. All are exposed and, with the exception of Gly35, close to site 2 used by IL-6 binding to gp130 in the hexamer model. The reduction in activity observed by the mutation of Gly35 to Phe may be due to indirect longer range effects resulting from the insertion of a large hydrophobic side chain.

In addition to the mutations described above, a chimer consisting of human IL-6 with murine residues 43–55 has reduced signalling activity but unaltered affinity for IL-6r (Ehlers et al., 1994). Examination of the hexamer model suggests that this region of IL-6 is important for interaction with the second molecule of gp130 via site 3. Other mutants consistent with site 3 in the hexamer model are located at the N-terminus of helix D. Trp157 to Arg and Asp160 to Arg (Paonessa et al., 1995) are both exposed and able to interact directly with the second gp130 receptor in this model. The other residues in this region (Gln159 to Glu and Thr162 to Pro/Thr162 to Asp (Brakenhoff et al., 1994; de Hon et al., 1995)) are both buried and consequently may affect gp130 binding indirectly.

Our model predicts additional interactions between two molecules of IL-6 which stabilise the signalling complex. Based on this model we predict that the region Glu106 to Arg113 on IL-6 would interact with the same residues on an adjacent IL-6 across a local two fold axis of rotation. The details of these interactions are currently the subject of further investigation.

The structure of IL-6 has allowed further refinement of the hexameric model presented by Paonessa et al (1995) and has enabled a more detailed understanding of the available mutagenesis data. Since LIF, CNTF, Oncostatin M, and IL-11 all share gp130 as a common signal transducer and are predicted to have similar four helical structures it seems likely that a hexameric complex may be a common feature of signal transduction for this family of cytokines.

Materials and Methods

RecombinantIL-6 expressed in *E.coli* was refolded (Arcone et al., 1991) and purified with ion exchange and hydrophobic interaction chromatography. Purified IL-6 at 15 mg/ml was crystallised using hanging drop vapour diffusion from 1.8 M ammonium sulphate, 300 mM sodium potassium tartrate, in 100 mM pH 6.3 sodium citrate buffer. The largest crystals measured 0.6×0.4×0.2 mm and took up to 2 months to grow at 4° C.

Intensity data were collected using a Rigaku R-Axis II image plate on a RU-200 X-ray generator running at 5 kW with mirror focussing optics. Examination of the symmetry of reduced rotation data and the pattern of systematic absences on rotation images clearly indicated crystals were of space group P3121 or P3221 with cell parameters a=49.7 Å and c=122.0 Å. All high resolution data sets were collected at −168° C. on crystals soaked in 20% glycerol as a cryoprotectant. These crystals were found to be highly ordered, diffracting to beyond 1.9 Å resolution. The image plate data were processed with DENZO (Otwinowski, 1993) then scaled with ROTAVATA and AGROVATA (4, 1994) giving statistics listed in Table 1.

TABLE 1

IL-6 data reduction and phasing statistics for a native crystal and single derivative.

|  | Native | Derivative |
| --- | --- | --- |
| Resolution | 10.0–1.9 | 10.0–2.4 |
| Number of observations[a] | 100519 | 31588 |
| Number of unique reflections | 14002 | 7203 |
| Completeness (%) | 97.6 | 99.1 |
| Reflections with I > 3 σI (%) | 93.0 | 95.1 |
| R-merge[b] | 0.031 | 0.029 |
| Fractional isomorphous difference[c] |  | 0.264 |
| Cullis R-factor[d], acentric/centric |  | 0.57, 0.53 |
| Phasing power[e], acentric/centric |  | 2.22, 1.84 |
| Figure of merit |  | 0.57 |

[a]Number of observations after pairing partial reflections in adjacent images.

b. R-merge = $\sum |I_j - \langle I \rangle| / \sum I_j$ where $I_j$ is the intensity of a measured observation and $\langle I \rangle$ is the average of all symmetry equivalents of that observation.

c. Fractional isomorphous difference = $\sum ||F_{PH}| - |F_P||/\sum |F_P|$ where $F_P$ is the native structure factor amplitude and $F_{PH}$ that of the derivative.

[d]Cullis R-factor is the lack of closure residual/isomorphous difference.
[e]Phasing power = RMS $F_H$/lack of closure, where $F_H$ is the calculated heavy atom contribution.

The structure was solved using single isomorphous replacement with anomalous scattering (SIRAS) prepared by soaking the crystal in 1 mM potassium tetrachloroaurate (III) for 24 hrs at 4° C. The gold heavy atom derivative gave a single site located using isomorphous difference Pattersons and then confirmed with a clear signal in the anomalous difference Patterson. Refinement of the heavy atom occupancy, position and isotropic thermal parameters followed by calculation of phases was performed using MLPHARE (Otwinowski, 1991) as part of the CCP4 suite of programs (4, 1994). The phasing statistics reported by MLPHARE are shown in Table 1.

Figure 6:
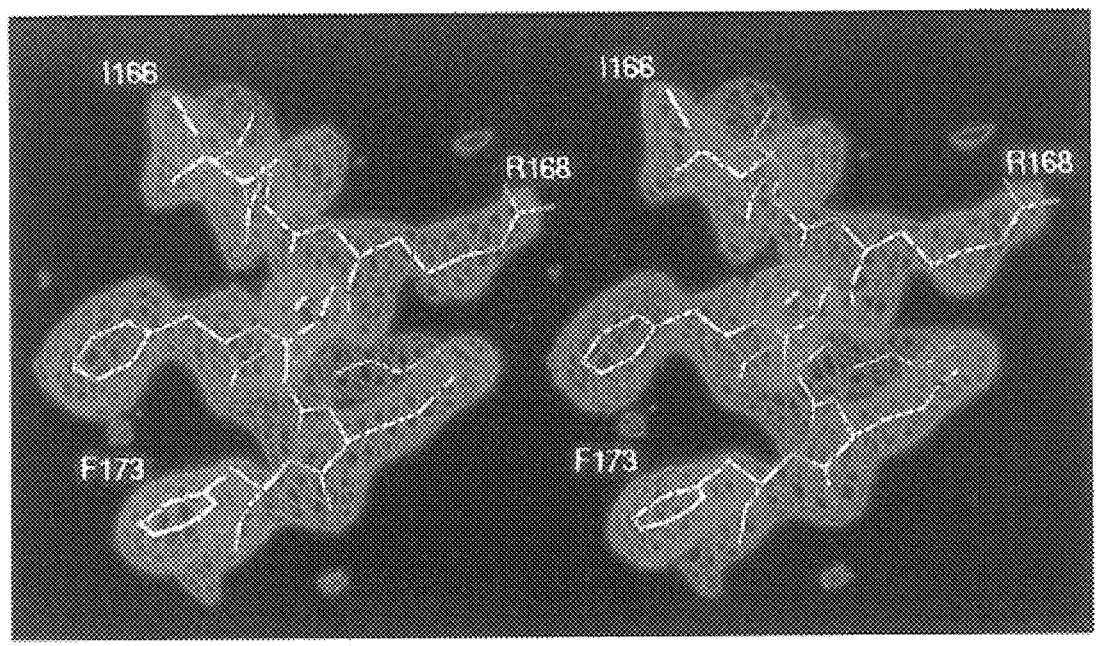
FIG. 6: A stereo plot of a good region of IL-6 2.8 Å electron density phased using single isomorphous replacement with anomalous scattering and solvent flattening.

Space group ambiguity was resolved by examining 2.8 Å electron density maps phased including the anomalous data. Space group P3121 gave a clear protein-solvent boundary with density that corresponded well with the secondary structural elements of the related cytokine, hG-CSF (Hill et al., 1993). The related space group P3221 gave no recognisable protein features. Electron density was further improved with solvent flattening (Wang, 1985) giving high quality 2.8 Å maps (FIG. 6) that were used to build an initial model using QUANTA (Biosym/MolecularSimulations, San Diego, Calif.) and O (Jones et al., 1991). The model and electron density maps were improved with repeated rounds of least squares refinement using PROLSQ (Hendrickson, 1985), SIGMAA weighting (Reed, 1986) and phase combination at 2.4 Å. Prior to refinement of the model, 5% of the reflections were removed to monitor the free R-value (Brunger, 1992). After later data collections these same free R-value reflections were maintained so that at the end of refinement these reflections represent a reliable, unbiased indication of the quality of the model. Conventional least squares refinement with PROLSQ and simulated annealing in XPLOR (Brunger et al., 1987) were both used to give a final model with an R-value of 21.3% for all data in the range 8.0–1.9 Å and a free R-value of 27.7%. The RMS deviation of the model from ideal geometry is 0.017 Å for bond lengths, 0.026 Å for angle distances and root mean square difference in the thermal parameters between bonded main chain atoms is 1.5 Å2 and for side chain atoms is 3.3 Å2. The average B factor for main chain atoms is 24.8 Å2 and for side chains is 28.4 Å2. The Ramachandran plot calculated with PROCHECK (Laskowski et al., 1993) no residues with backbone torsion angles in disallowed regions and 95.2% in the most favoured regions.

The final model consists of 157 residues (1414 atoms) with 121 ordered water molecules, 3.5 sulphates and 0.5 tartrates. In the final electron density maps residues 1–18, 52–60 and side chains Asn61, Asn63, Glu81, Lys131, Asn132 are disordered and have not been modeled.

NMR Solution Structure of IL-6

We have previously reported on the sequence-specific assignments, secondary structure analysis, and overall topological fold for IL-6 (Xu et al., 1996), providing experimental confirmation for at least some of the structural predictions made for IL-6. Herein we report the high resolution NMR solution structure for IL-6 which, together with the accompanying report on the X-ray structure determination (Somers et at., 1996), provides the first experimental tertiary structure information on IL-6.

Note re nomenclature: Amino acids in the IL-6 sequence are referred to in the following discussion of the NMR solution structure in a manner slightly different than that employed in the foregoing discussion of the crystallographic structure. The same amino acid in the IL-6 sequence is referred to in the following discussion by a residue number which is one greater than that used in the foregoing discusssion to denote the same amino acid. For example, Ser21 in the foregoing discussion of the crystallographic structure is the same as Ser22 in the following discussion of the NMR solution structure. This difference is due to the fact that the N-terminal methionine in the recombinant human IL-6 sequence is assigned residue number −1 in the crystallographic discussion and is assigned residue number 1 in the NMR discussion.

Results

Experimental Restraints

A total of 2966 interproton distance restraints were obtained from 3- and 4-dimensional NMR spectra of either singly ($^{15}$N) or doubly labeled ($^{15}$N, $^{13}$C) IL-6. This set is comprised of 899 intraresidue, 838 sequential 786 medium-range, and 443 long-range restraints, yielding an average distance restraint-per-residue number of 18. Included within this set are 138 hydrogen bonding restraints derived from NMR observation of 69 backbone amide hydrogens which showed slow exchange with $D_2O$ and were assigned hydrogen bonding partners in α-helical segments in conjunction with local NOE patterns. Essentially all restraints are localized to residues 21–185; we have previously reported that the amino-terminal 20 residues of IL-6 are extremely flexible, as evidenced by observed $^{15}$N $T_2$ values (Xu et al, 1996), and thus fail to yield any restraints useful for 3D structure determination.

In addition, other experimental restraints were employed in subsequent calculations. A total of 83 dihedral angles were defined from $^3J_{HN, H\alpha}$ values obtained as described under "Methods". Obtaining a greater number of angular restraints was precluded largely by the lack of spectral dispersion of this four-helix bundle. Only relatively few stereospecific assignments could be made largely due to the hydrodynamic characteristics of IL-6. For example, the average $^{15}$N $T_2$ values observed in the core region of IL-6 was about 40 ms; such behavior results in very poor magnetization transfer via scalar coupling in NMR experiments. This characteristic of IL-6 not only made resonance assignment difficult (Xu et al., 1996), but also made obtaining stereospecific assignments for methylene protons impossible.

However, due to the relatively fast rotational behavior of methyl groups located at the terminus of sidechains and their consequently improved spectral traits, some stereospecific assignments were made for certain well resolved leucine δ-methyl moieties. In total, stereospecific assignments for the δ-methyls of 10 out of 23 leucine residues were obtained as described under "Methods". While few in number, these select assignments proved to be especially valuable since they were found buried within the folded core of IL-6 and thus provided many stereospecific interhelical NOE's.

Calculations

A family of 75 embedded substructures were generated using distance geometry (Brunger, 1993) followed by simulated annealing, regularization and refinement (Nigels et al., 1988). An iterative procedure was used in the latter three steps to successively introduce an increasing number of NOE distance restraints. The procedure also examines any NOE violations in the family of interim structures and attempts to adjust their classification (strong, medium or weak) to relieve the violations. This process was repeated until all 2966 NOE distance (including 138 hydrogen bond) and 83 torsion angle restraints were used, producing the final set of structures.

A final ensemble of 30 structures was obtained that did not exhibit either any NOE distance violation greater than 0.3 Å or any torsional angle violation greater than 5 degrees. The average structure was calculated by superimposing all main chain N, $C_\alpha$, C atoms of the 106 residues defining the core 4-helix bundle (FIG. 7; helix A:21 to 47 in green; helix B:81 to 106 in blue; helix C:109 to 131 in yellow; helix D:156–185 in red). Assignment of the helical residues, including those of residues 143 to 154 for helix E, is based on an evaluation of the average structure using the program Procheck 3.0 (Laskowski et al., 1993) to include all residues with secondary structural assignments of "H" or "h".

Description of the NMR-derived Structures

Figure 7:
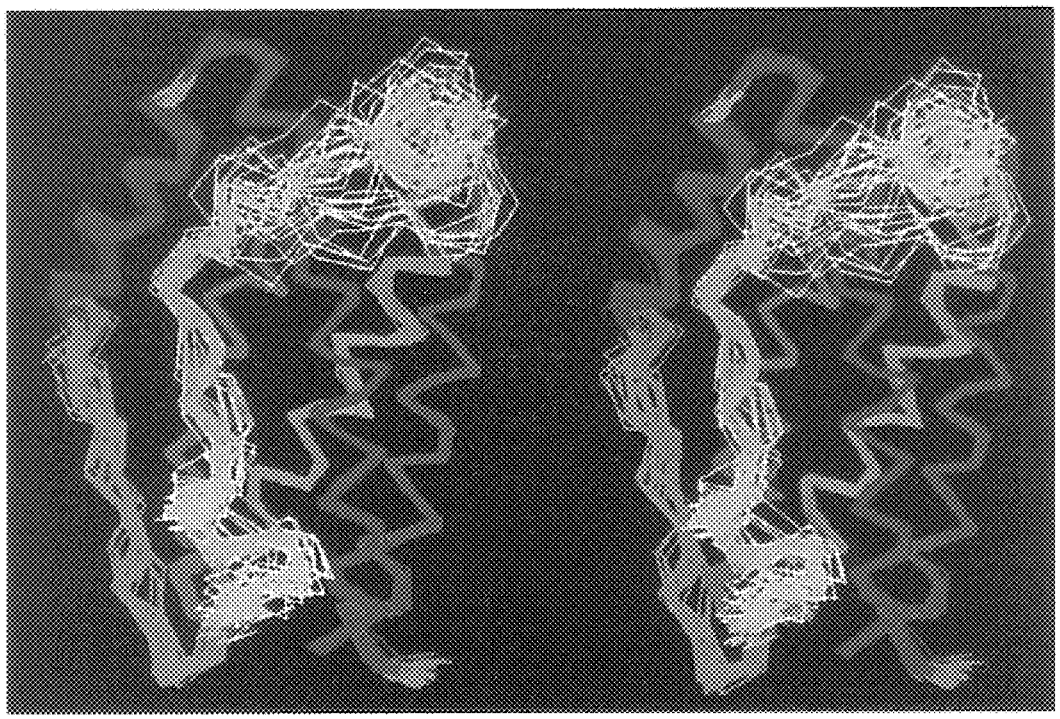
FIG. 7: Stereo diagram illustrating best-fit superpositions of the Cα traces of the 30 structures of IL-6 in the final ensemble. The color coding scheme is as follows: Helices A-E are respectively green, blue, yellow, red, and magenta. The AB and CD crossover loops are white and grey, respectively.

We have previously reported that the overall topology for IL-6 in solution is that of long-chain, up-up-down-down left-handed 4-helix bundle with long loops connecting helices A and B as well as C and D (Xu et al., 1996). The overall results of the high resolution NMR structure of IL-6 further refine these observations. FIG. 7 shows a stereo diagram of the $C_\alpha$ traces of the 30 structures constituting the final ensemble and illustrates the quality of the ensemble. The precision of the final set is striking, particularly in terms of the packing and orientation in the core (A–D) helices. The root-mean squared difference (RMSD) from the average structure of main chain atoms in the 30 4-helix cores is only 0.44 Å; the RMSD for all non-hyarogen atoms in the core region increases to 0.96 Å. Most of the observed conformational variability among the 30 structures is localized to the crossover loop regions (shown in white), particularly at the amino terminal portion of the AB loop. The RMSD from the average structure for all main chain atoms in the 30 structures is 1.0 Å and for all non-hydrogen atoms is 1.5 Å.

Figure 8:
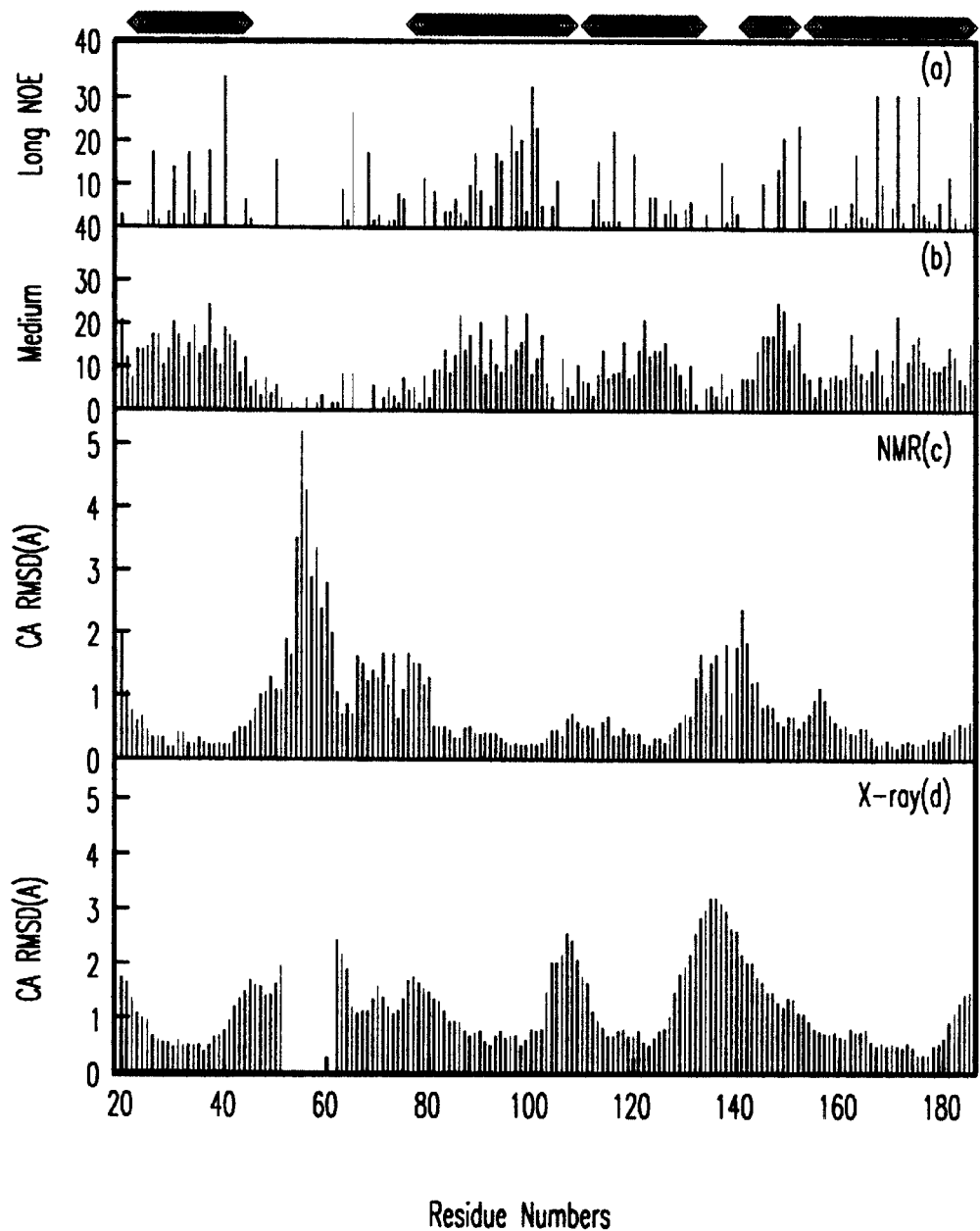
FIG. 8: Per-residue Structural Statistics from the ensemble of 30 NMR-derived structures. Panels A and B: Number of long and medium range NOEs, respectively, per residue; Panels C and D: Cα RMSD distributions for the NMR and X-ray (Sommers et al; 1996) structures of IL-6.

The quality of the high resolution NMR structures can be assessed more quantitatively in several ways. For example, the distribution of NOE restraints over the protein and their correlation to RMSD in $C_\alpha$'s can be evaluated (FIG. 8). Panels (a) and (b) give the number of NOE restraints per residue for long- and medium-range enhancements, respectively. The five helices from the NMR refinement are shown at the top in the order of A, B, C, E, and D. As one would expect, the number of NOE restraints is greater in helical regions. The characteristic helical periodicity in long-range NOEs is also evident, in particular for helices A, B and D. In order to illustrate the effect of NOE restraints on the quality of the final structure, we show the $C_\alpha$ RMSD from the NMR refinement in panel (c). As expected, there is an inverse correlation such that regions with a higher number of NOE restraints give smaller RMSD and thus a better defined structure. Conversely, the region at the beginning of the AB loop has RMSD values significantly higher than all other regions. This is also clearly shown in FIG. 7 as the top right corner of the stereo diagram where the white traces span the largest conformational space relative to other part of the protein. For comparison, we give the $C_\alpha$ RMSD calculated from the X-ray refinement (see companion paper) in panel (d). The beginning of the AB-loop is not evident in the X-ray structure, whereas all other regions show very good positive correlation with that of the NMR data in panel (c).

Figure 9:
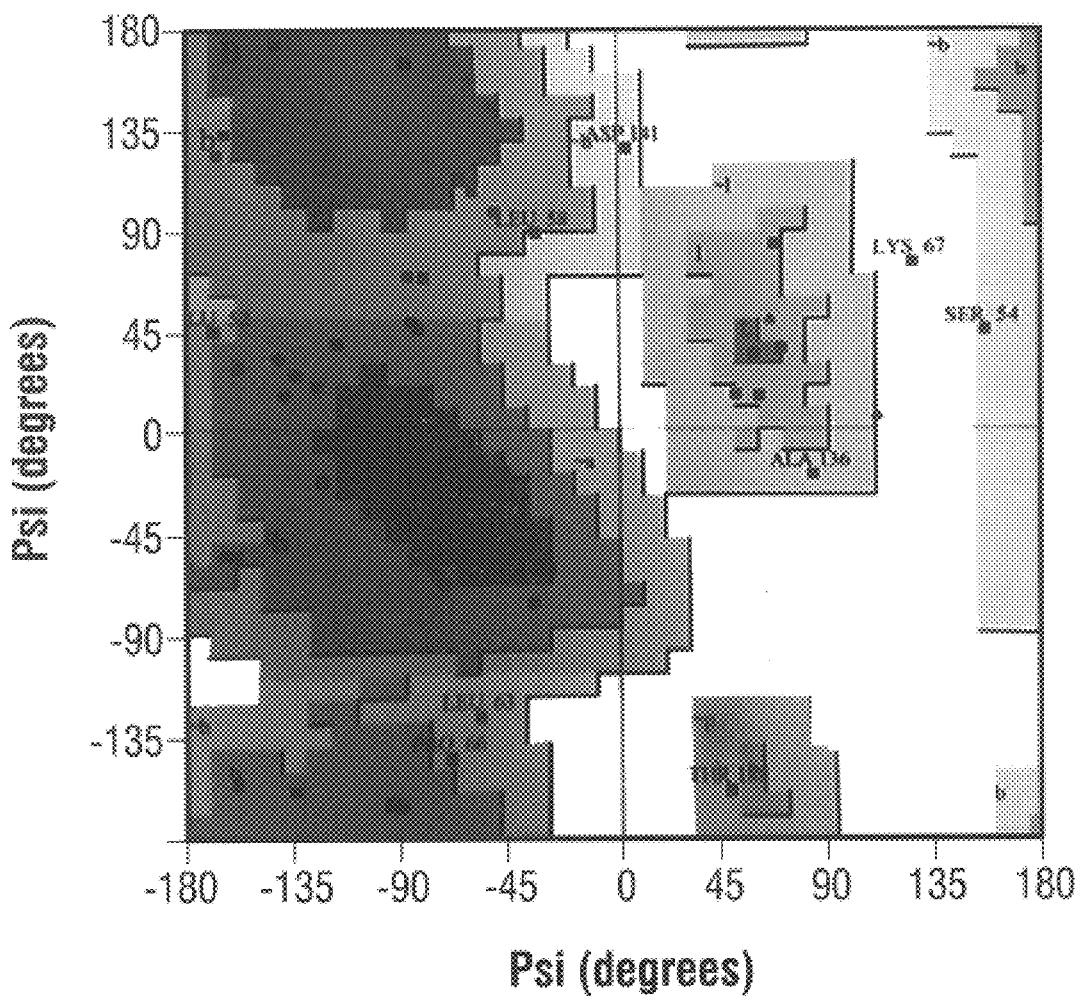
FIG. 9: Ramachandran $\phi/\psi$ plot for residues 21–185 of IL-6.

The quality of the NMR-derived ensemble can also be assessed energetically. Table 2 lists relevant energetic characteristics. As can be seen, the ensemble appears to be energetically reasonable with no NOE violations greater than 0.3 Å and with acceptable covalent geometry. The higher energetic values in the energy-minimized structure are due to two NOE violations greater than 0.3 Å and three torsion violations greater than 5 degrees. A Ramachandran $\phi/\psi$ plot for the energy minimized NMR average structure (FIG. 9), as calculated with Procheck 3.0 (Laskowski et al., 1993), shows good clustering of residues in the most favorable α-helical region ($\phi/\psi=-60°/30°$) as expected for a 4-helical bundle protein. A total of 73% of residues are in the most favored regions [A,B,L] while another 21% are in the additional allowed regions. An additional 5% of residues fall within generously allowed regions and only one residue (K67) is in a disallowed region.

Figure 10:
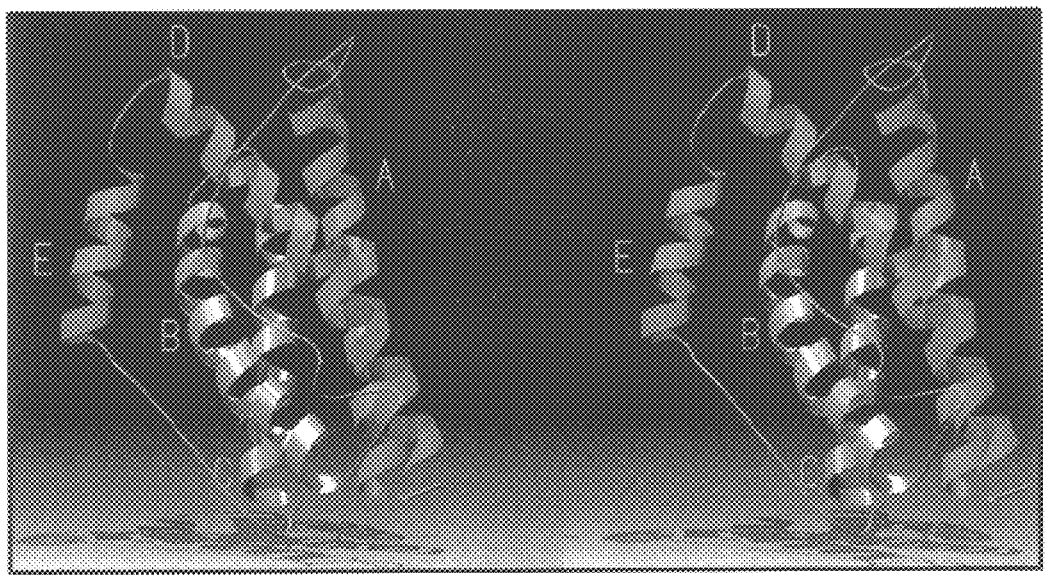
FIG. 10: Stereo image of the averaged and minimized NMR structure of IL-6. Only residues 21–185 are shown and individual helices are labeled.

The high resolution NMR structures of IL-6 show a number of additional structural features of interest. The A helix (residues 21 to 47) shows a pronounced "kink" (of 37°) starting in the vicinity of residue 42. The existence of a kink correlates with the fact that residues 39 and 40 have some missing (i,i+4) hydrogen bonds that are characteristic of α-helices. The amino terminal portion of the AB crossover loop is stabilized by disulfide bonding between C45 and C51 and a hydrogen bond between C45 and E52. The characteristic packing of the AB crossover loop over the top of the D helix and its attached CD loop is evident (FIG. 7 and FIG. 10; Sprang and Bazan, 1993). The C-terminal portion of the AB crossover loop has consecutive 5-turn (residues A69–C74) and 3-turn (residues Q76–F79) elements with additional stabilization through tie C74–C84 disulfide bond. A pronounced "kink" (of 24°) in the B-helix (residues 81–104) is observed although there is no perturbation of helical (i,i+4) hydrogen bonding. Helices B and C (residues 110–130) are connected by a 5 residue turn. The CD crossover loop has a 3-turn element at its amino terminus (A131–L134) continuing on into an extra-core helix (helix E; residues 142–153). The amphipathic E helix is stabilized through extensive side-chain interactions with the core bundle, most particularly with the B helix. These interactions contribute to the E helix being well defined relative to the rest of the CD loop in the ensemble of NMR structures. The high apparent flexibility at the start of the AB loop is, in contrast, the result of few side-chain interactions with the core bundle (FIG. 7). The D helix (residues 157–184) also shows a slight kink (of 17°) centered roughly in the middle of the helix.

Figure 11A:
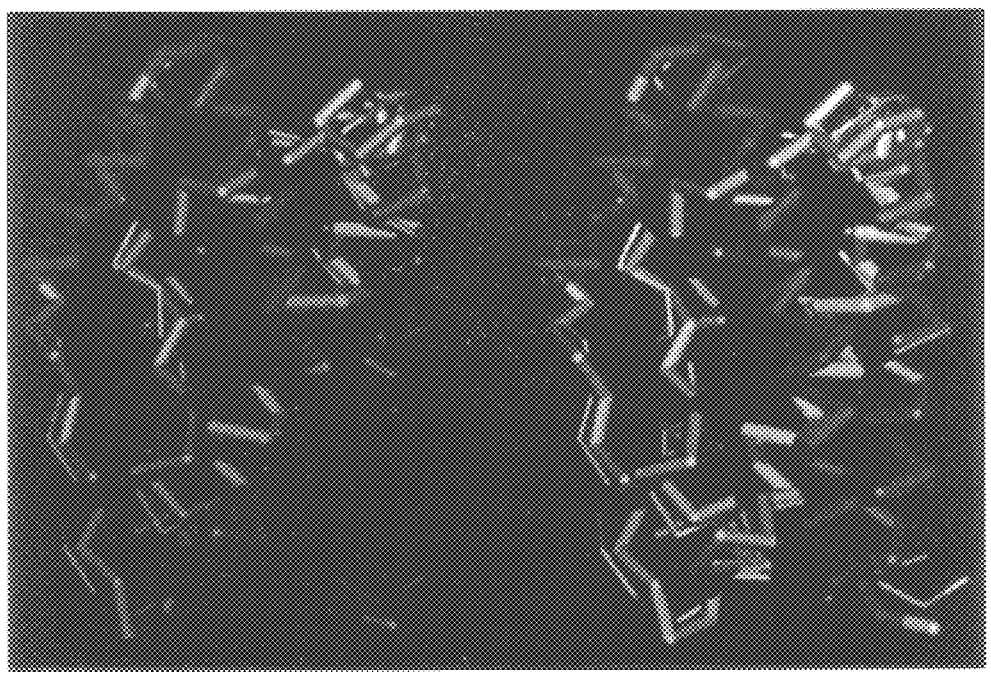
FIG. 11A: Best-fit superposition of the Cα atoms of the restrained minimized average NMR and the X-ray structures of IL-6. The color coding scheme is identical to that of FIG. 7. The averaged NMR structure is shown in thick lines while the X-ray structure is shown in thin lines.
Figure 11B:
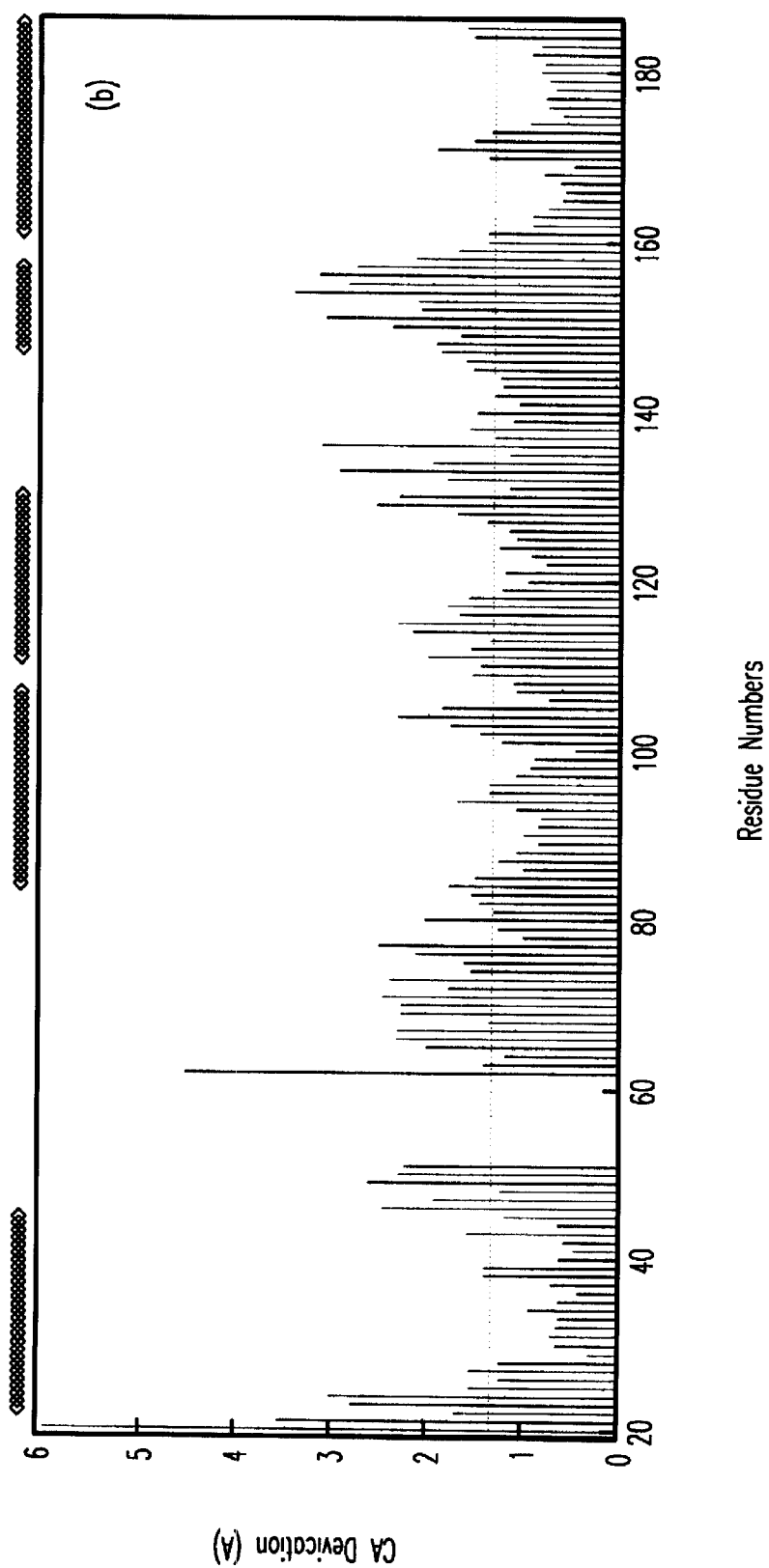
FIG. 11B: Plot of $C_\alpha$ Deviation (Å), i.e., distances ($C_\alpha$-$C_\alpha$ in Å) between NMR and X-ray determined structures of IL-6, by residue.

In FIG. 11A, the energy-minimized NMR average structure is compared to that determined by X-ray crystallography (Somers et al., 1996). The color coding corresponds to that used in FIG. 7 with the NMR structure in thick lines and the X-ray structure in thin lines. Electron density for residues 52 to 61 in the beginning of the AB loop is not interpretable in the X-ray data. This corresponds to the hypervariable regions in the NMR-derived ensemble as shown in FIG. 7. For the most part, the core A, B, C and D helices between the two methods match well with each other (Table 3). Any differences between the structures lie mostly in the loops, at the ends of the helices, and in the E-helix. Interestingly, the kinks in A and D helices observed in the NMR ensemble averaged structure are not evident in the X-ray structure. These differences are revealed more quantitatively in FIG. 11B where the $C_\alpha$-$C_\alpha$ distances between the NMR and the X-ray is plotted. Observed difference range from 0.3 to 6.0 Å (with an average of 1.6 Å indicated by the dotted line) where larger deviations are mainly localized in the end of helixes and in helix E where there is a shift in the whole helix in the X-ray relative to NMR. The RMSD in main chain N, $C_\alpha$ and C of the core helices between the averaged NMR and X-ray structures is 1.33 Å as compared to the value of 0.44 Å among the 30 NMR structures. Thus, the structure of IL-6 determined by the two methods agree remarkably well.

The NMR structure also yields interesting insights into the phylogenetics of IL-6, FIGS. 12A & 12B show the multiple sequence alignments of IL-6 from nine mammalian species (human (SEQ ID NO: 1); bovine (SEQ ID NO: 2); cat (SEQ ID NO: 3); rhesus (SEQ ID NO: 4); sheep (SEQ ID NO: 5); rat (SEQ ID NO: 6); mouse (murine)(SEQ ID NO: 7); sea otter (SEQ ID NO: 8); and pig (SEQ ID NO: 9). As was previously reported (e.g. King et al. 1995), all species except mouse and rat show reasonable levels of similarity in their amino acids sequences. It has been suggested that sequence differences in rat (SEQ ID NO: 6) and mouse (SEQ ID NO: 7), as compared to the other mammalian species, could account for the inability of murine IL-6 to elicit a response from human cells while IL-6 from all species can elicit a response from murine cells (see below). Inspection of FIGS. 12A & 12B shows that 31 amino acids residues are invariant across all species in residue range 21–185. Two thirds of these invariant residues fall within helices in human IL-6, four are Cys residues, and the rest lie within the AB loop (Table 4). Evaluation of FIGS. 12A & 12B in terms of the tertiary structure of human IL-6 indicates that most gaps/insertions fall within two regions: the start of the CD loop (up to start of helix E) or the short turn between helices B and C where an additional Lys residue is inserted in the rodent strains. Interestingly, bovine (SEQ ID NO: 2), porcine (SEQ ID NO:9), and ovine IL-6 (SEQ ID NO: 5) may have a shorter A helix given the presence of a Pro four residues into the presumed start of the helix. Despite some interspecies variations, however, the essential features of the tertiary structure of human IL-6 should be retained in all mammalian forms.

Discussion

This study presents the first high-resolution NMR structure of a long chain 4-helix bundle cytokine reported to date. As a protein of 185 amino acids with a high α-helical content, IL-6 presented unique challenges for NMR-based structure determination. Spectral dispersion, even in multi-dimensional NMR experiments, was poor and magnetization transfer was problematic, especially in terms of obtaining stereo-specific assignments. Nonetheless, a sufficient number of restraints per residue, including a limited number of important stereo-specific assignments, allowed the generation of an ensemble of structures with geometric and energetic characteristics that compare very favorably to other NMR-based structure determinations of substantially smaller proteins. The high quality of the NMR-derived structure of IL-6 is due, in no small part, to the intrinsic packing of the long helices into a 4-helix bundle, thus compensating for what would otherwise be significant methodological limitations.

The averaged structure from the NMR-derived ensemble relates well to the NMR/X-ray structures of other long-chain 4-helix bundle cytokines, including G-CSF (Zink et al., 1994), LIF (Robinson et al., 1994), CNTF (McDonald et al., 1995), G-CSF (Hill et al., 1993), and GH (Ultsch et al., 1994). The structure of IL-6 retains many of the structural characteristics ascribed to this family of proteins that distinguish them from their short-chain counterparts(e.g. IL-3, IL-4, IL-5, and M-CSF; Sprang and Bazan, 1993). These include the length of helices in the bundle, the presence of short extra-core α-helices instead of extra-core β-sheets, and a characteristic AB over CD loop packing. Within this family, certain structural features distinguish IL-6 from other family members. For example, the extra-core mini-helix es of the neuropoietic cytokines LIF and CNTF are localized to the AB loop, whereas these helices are present in the CD loop in IL-6, as in IFN-β (Senda et al., 1992). In the case of IL-6, one of the two potential N-linked glycosylation sites (at $N^{46}$ and $N^{145}$) is located, though not utilized (Orita et al., 1994), within this helix. This is likely due to the fact that N145 is on the face of the E helix interacting with the B helix. While most members of this family contain variable length (9–20 residues) N-terminal stretches preceding helix A (IL-6 has a mobile N-terminal span of 20-amino acids), CNTF and OSM have C-terminal sequence extensions following the D-helix. Like LIF, IL-6 has a very short BC loop but a long AB loop as in G-CSF.

The NMR-determined structures of IL-6 compare favorably to that determined by X- ray crystallography (Somers et al., 1996). As summarized in Table 3 and in FIGS. 11A & 11B, a comparison of interhelical distances and angles shows excellent agreement between the average NMR an the X-ray structures. Comparisons of per residue RMSD between the structures is also quite good with the main differences being observation of the entire AB loop and reduced values for $C_\alpha$RMSDs in the short BC loop in the NMR-derived structure. Both methods give comparable values for the B helix kink angle and the helical packing skew angle. However, the NMR-derived structure exhibits discernable kinks in the A and D helices absent in the X-ray structure. These latter kinks are reminiscent of the A and D helix kinks observed in the structures of the neuropoietic cytokines LIF and CNTF (Robinson et al., 1994; McDonald et al., 1995) which have been suggested to be important for receptor engagement (McDonald et al., 1995). However, it should be noted that the A helix kink in the NMR-derived structure of IL-6 is placed near the end of the helix in contrast to the middle as in both LIF and CNTF.

Mapping interspecies sequence differences onto the structure of IL-6 yields two interesting sets of observations. First, over the range of residues for which structure is observed (residues 20–185), 31 residues are absolutely conserved (Table 4). Of these, four are Cys residues comprising two disulfide bonds and 18 others are located within α-helices. As noted in Table 4, most of these latter 18 residues have been implicated either in core helical packing (Xu et al., 1996) or in receptor binding (see below) The remaining 9 conserved residues all lie within the AB crossover loop. No conserved residues are present in the CD loop, except for two in the extra-core helix E. In contrast, most gaps observed in the multiple alignment fall in the CD loop prior to the E-helix. Since this region has yet to be implicated in receptor binding or in maintaining the 4-helix bundle topology, it is at least teleologically satisfying as a locus of interspecies variation without significant structural or functional consequence.

The biological effects of IL-6 are mediated through the ordered formation of a heteromeric receptor complex, initiated by the binding of IL-6 to the extracellular domain of IL-6Rα. The IL-6/IL-6Rα complex is then capable of binding gp130. Analysis of the determinants on IL-6 which mediate formation of a hexameric receptor complex have been pursued by a combination of epitope-mapping of antibodies and site-directed mutagenesis (Savino et al., 1993,1994; Paonessa et al., 1995; Brakenhoff et al., 1995). To date, at least three sites have been identified on IL-6 which mediate binding to different components of the receptor complex. The determinant for IL-6 binding to IL-6Rα is termed site I and is composed of residues at the beginning of the A helix, the C-terminal end of the D helix, and select residues towards the end of the AB loop (Savino et al., 1993,1994). Two additional sites (II and III) are responsible for interactions with two different molecules of gp130

(Paonessa et al., 1995; Brakenhoff et al., 1995). Site II is composed largely of residues in helices A and C while site III is composed of residues at the amino-terminus of the AB loop, at the carboxy-terminus of the CD loop (just after the end of helix E) and at the N-terminus of the D-helix. While the details of IL-6 interactions with other components of the receptor complex, including the definition of a new site IV mediating an IL-6/IL-6 interaction in the hexameric complex, are discussed more fully in the accompanying report (Sommers et al., 1996), it is of interest to note that a portion of site III includes residues which, as determined by NMR, are located within a highly mobile region of the AB loop (see FIG. 7).

Figure 13:
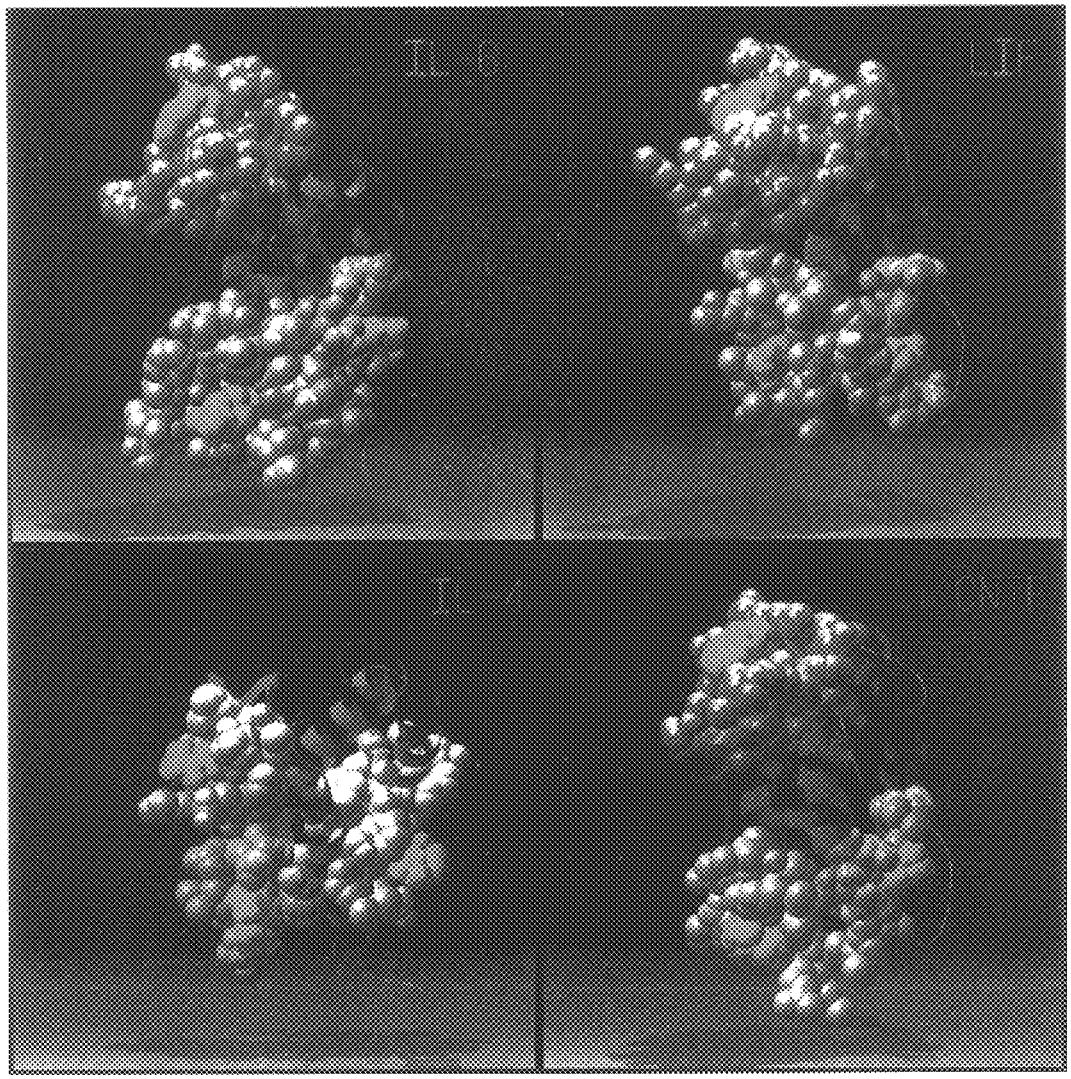
FIG. 13: Conversion of topology and functionality of receptor binding sites in 4-helix bundle cytokines. Receptor binding sites on IL-6, LIF, CNTF, and IL-4 were generated from published mutagenesis data (Table 5) as described under "Methods". The three dimensional structures of each cytokine were superimposed as described and are viewed from an identical perspective. For all cytokines except IL-4, the specificity conferring site (I) is shown in white CPK while the accessory sites (II and III) are shown in pink and blue CPK, respectively. This coding is reversed for IL-4. The bolded residue for each site listed in Table 5 is shown here in red.

It is clear that other cytokines also utilize at least three sites on their surface for receptor engagement. Indeed, Panayotatos et al. (1995) have proposed that long-chain helical cytokines share, in addition to a common topological fold, a conserved spatial arrangement of receptor binding sites. Moreover, the functionality associated with each site, in terms of the receptor component bound at that site, is also conserved. This hypothesis is potentially important since a common disposition of functionally equivalent receptor sites would require a similar mechanism of receptor engagement. Thus, the specificity-conferring site I is proposed to be topologically equivalent in CNTF and LIF when mapped onto the available X-ray structures. Sites II and III, which bind the accessory receptor components gp130 and LIF-R, are similarly conserved. This hypothesis was also extended to IL-6 utilizing a model derived by homology to G-CSF. The high resolution NMR structure of IL-6 allows us to lend additional experimental support for this hypothesis. We have also been able to extend this hypothesis to a short chain cytokine, IL-4. Table 5 summarizes the available mutagenesis data which defines sites I, II, and III in IL-6, LIF, CNTF, and IL-4. FIG. 13 illustrates the results of mapping this data onto the available structures (as described under "Materials and Methods") and shows the conserved spatial disposition of the three sites. FIG. 13 also illustrates that the functionality associated with each site is conserved in the long chain cytokines but reversed in IL-4. The receptor binding sites in IL-4 are more closely spaced presumably due to the shorter helical lengths. Together, the apparent topological conservation of receptor binding sites within both short-chain and long-chain cytokines strongly suggests a divergent evolutionary progression of cytokines and their receptors, as opposed to convergence to common tertiary motifs.

Materials and Methods
1. NMR spectroscopy

A complete set of resonance assignments, secondary structure analysis, and a gross topology for IL-6 by NMR have been reported previously (Xu et al., 1996). For the present studies, a 1.3 mM sample of purified and uniformly $^{15}$N- or $^{15}$N, $^{13}$C-labeled recombinant IL-6 were prepared in 10 mM Mes pH 6.1, 200 mM MgSO4, as described previously (Xu et al., 1996). All NMR experiments were performed in 10% $D_2O$/90% $H_2O$, except for the 4D-$^{13}$C, $^{13}$C edited NOESY experiment, which was performed in 100% $D_2O$. NMR experiments were carried out as previously described (Xu et al., 1996). Distances constraints were obtained from the analysis of data from a battery of experiments including $^2$D-$^1$H,$^1$H-NOESY (aromatic region only), 3D-$^{15}$N edited-NOESY, simultaneous$^{15}$ $N^\beta$/C-edited NOESY (at 100 ms mixing time) (Pascal et al., 1994, Xu et al., 1995) and 4D-$^{13}$C, $^{13}$C-edited NOESY experiments (Clore et al., 1991; Zuiderweg et al., 1991, Vuister et al., 1993). 2D-HSQC-J experiment (Kay et al., 1990) was performed to measure backbone $^3j_{HN-H\alpha}$ values and thus define φ angle constraints. A 3D-HNHA-J experiment (Vuister & Bax, 1993, Garrett et al., 1994) was carried out to confirm and expand the number of φ angle constraints. Hydrogen bonds were determined from a series of 2D HSQC experiments after re-dissolving a sample of lyophilizedIl-6 in $D_2O$ and monitoring over time. A combination of 2D-constant time (Powers, R. et al., 1993) methyl-relay (Kay et al., unpublished), 3D-long-range-CCJ (Bax et al., 1992, 1994), 3D-$^{15}$N edited NOESY, and 4D-$^{13}$C,$^{13}$C edited-NOESY (Clore et al., 1991; Zuiderweg et al., 1991, Vuister et al., 1993) experiments Were used to obtain δ-methyl stereospecific assignments for leucine residues. Triple resonance experiments that ultimately detect NH magnetization were recorded using enhanced sensitivity pulse field gradient methods (Muhandiram et al., 1994, Kay 1995). Quadrature detection in all of the indirectly detected dimensions was achieved via States-TPPI. All data were processed with nmrDraw and nmrPipe programs (Delaglio et al, 1996) and all spectra were extended in the heteronuclear dimensions by forward-backward linear prediction (Zhu & Bax, 1992) prior to apodization and zero filling to double the time domain data points. For HMQC-J experiments, Varian VNMR software was employed for spectral processing. All data analysis, spectra peak picking and plotting were performed with the psc and pipp programs (Garrett D., 1991, D. S. Garrett unpublished).

Stereospecific assignments of the δ-methyls of leucines were obtained as follows: First, we employed the 3D-long-range CCJ experiment where δ-methyl cross peak intensities are dependent upon $^3J_{c_\alpha-c_\delta}$ according to the equation $|I_{cross}/I_{diag}|^{1/2}=\tan(2\pi\tau^3J_{c_\alpha-c_\delta}$ and $2\tau=/^1Jcc=29.4$ ms )(Bax et al., 1994). Using this equation, the χ2 torsion angle constraints were grouped in two sets (180° and 60°). Next, a combination of intraresidue peak intensities from NOESY spectra (Powers et al., 1993) were employed for initial stereospecific assignments and further used to assign medium and long range NOEs.

Distance constraints were obtained from 3D-$^{15}$N and 3 D/4D-$^{13}$C heteronuclear-edited NOESY experiments (100 ms mix time) as well as from 2D-$^1$H,$^1$H-NOESY experiments (evaluated in the aromatic region only). Crosspeak intensities were classified as strong, medium and weak using contour levels for calibration with the corresponding distance constraints of 1.8 to 2.5 A, 1.8 to 3.3 A, and 1.8 to 5.0 A respectively. The lower bound for interproton distances was set to 1.8 A which is the sum of the van der Waals radii of two protons. The upper distance restraint, when involving non-stereospecific methylene protons, aromatic protons, and methyl protons [which were replaced by the appropriate pseudoatoms for center averaging (Wuthrich et al., 1983)] had an additional 0.5 A was added (Clore et al., 1987; Wagner et al., 1987).

$J_{NN-H_\alpha}$ coupling constants from 2D-HMQC-J and 3D-HNHA-J experiments were extracted using either the program described by Forman-Kay et al. (1990) or by Vuister and Bax (1993). Values less than 5 Hz were assigned as $-30° < \phi < -90°$ torsion angle restraints. Values larger than 8 Hz were assigned as $-60° < \phi < -180°$ torsion angel restraints.

2. Structure Calculations and Refinement

NMR structure refinements and analysis were carried out using X-PLOR version 3.1 (Brunger, 1993) with topallhdg.pro and parallhdg.pro as the topology and parameter sets, respectively. The standard NMR refinement protocol recommended in XPLOR was followed. This included three stages: (1) Partial substructure distance geometry embedding to generate 75 initial structures, (2) Simulated annealing starting at a temperature of 2000K with variously scaled force constants and parameters to a final temperature of 100K; (3) Refinement by further simulated annealing starting at 1000K with 2000 cooling steps to a final temperature of 100K. This protocol gave 20 structures (27%) that showed no NOE distance violation greater than 0.3 Å and no dihedral angle vilation greater than 5 degrees. To increase the number of such acceptable structures, the refinement was continued with a gentle cycle of simulated annealing that started with a temperature of 300K, slowly cooling down to 100K in 20000 steps. Addition of this last cycle of refinement yielded a final ensemble of 30 structures that showed no NOE distance violation greater than 0.3 Å and no dihedral angle vilation greater than 5 degrees.

3. Other Techniques

Multiple sequence alignments were performed, as appropriate, according to Needleman and Wunch (1970) and Feng and Doolittle (1987) as implemented in QUANTA (MSI Inc.). Raytraced images were generated using the RAYSCRIPT patch to MOLSCRIPT with subsequent rendering with the program RAYSHADE. The algorithm of Chothia et al. (1981) as implemented in CHARMM (Brooks et al., 1983) was used to analyze the packing of the helices in the refined structures.

Binding sites on IL-6, CNTF, LIF, and IL-4 for their respective receptor components were defined as follows. The structure of human CNTF was constructed with the homology modeling package MODELER of Sali et al. (1995) based on the X-ray structure of murine LIF (Robison et al., 1994) and the sequence alignment of McDonald et al. (1995). The structures of murine LIF (1LKI) and human IL-4 (1BBN) were from the Brookhaven Protein Data Base. The structures of the cytokines were first superimposed according to the method of Sutcliffe et al. (1987), as implemented in QUANTA, with the IL-6 structure as the target. For each cytokine, all residues identified by site-directed mutagenesis as important for receptor binding were tabulated as in Table 5 and mapped onto the appropriate structure and visualized using the program VMD (Humphrey et al. 1996). A mapped residue centrally located within this subset of the molecular surface was then manually selected and a search performed, using the program RIBBONS (Carson, 1991) to define the minimum distance from this residue which encompasses all mapped residues for the site. Typically, the binding site was then defined by all atoms included within the area of the molecular surface inclusive of this distance from the central residue. However, if too few mutations were available, the distance derived for an analogous site on a related cytokine was employed. Thus, these receptor binding sites are only a crude approximation of the actual receptor sites.

TABLE 2

Structural, Energetic Statistics and Atomic rms Differences

| | Structural and Energetic Statistics | |
|---|---|---|
| | <SA> | (SA)r |
| rms deviations from exptl distance restraints (Å) | | |
| all (2966) | 0.0217 ± 0.0008 | 0.0261 |
| interresidue sequential ($\|i - j\| = 1$) (838) | 0.0257 ± 0.0014 | 0.0328 |
| interresidue short-range ($1 < \|i - j\| \leq 5$) (648) | 0.0192 ± 0.0018 | 0.0247 |
| interresidue long-range ($\|i - j\| > 5$) (443) | 0.0173 ± 0.0021 | 0.0240 |
| intraresidue (899) | 0.0203 ± 0.0014 | 0.0240 |
| H-bonds (138) | 0.0262 ± 0.0025 | 0.0253 |
| rms deviations from exptl dihedral restraints (deg) (83) | 0.3345 ± 0.0867 | 2.93 |
| rms deviations from idealized covalent geometry | | |
| bonds (Å) (2697) | 0.0027 ± 0.0001 | 0.004 |
| angles (deg) (4885) | 0.4533 ± 0.0066 | 0.632 |
| impropers (deg) (1341) | 0.3544 ± 0.0010 | 0.513 |
| Energetics | | |
| $E_{total}$ (kcal mol$^{-1}$) | 299.8 ± 9.5 | 619.9 |
| $E_{repel}$ (kcal mol$^{-1}$) | 30.4 ± 4.0 | 85.2 |
| $E_{NOE}$ (kcal mol$^{-1}$) | 70.1 ± 5.2 | 101.2 |
| $E_{cdih}$ (kcal mol$^{-1}$) | 0.6 ± 0.3 | 43.4 |
| $E_{bond}$ (kcal mol$^{-1}$) | 20.0 ± 1.4 | 38.4 |
| $E_{angle}$ (kcal mol$^{-1}$) | 152.9 ± 4.5 | 297.8 |
| $E_{improper}$ (kcal mol$^{-1}$) | 25.7 ± 1.5 | 53.8 |

| | Non-hydrogen Atomic rms Differences (Å)[a] | | | |
|---|---|---|---|---|
| | residues 20–185 | | secondary structure[b] | |
| | backbone atoms | all atoms | backbone atoms | all atoms |
| <SA> vs SA | 1.00 ± 0.20 | 1.48 ± 0.18 | 0.44 ± 0.05 | 0.96 ± 0.05 |
| <SA> vs (SA)r | 1.03 ± 0.21 | 1.58 ± 0.20 | 0.46 ± 0.06 | 1.00 ± 0.06 |
| (SA)r vs SA | 0.28 | 0.56 | 0.12 | 0.42 |
| SA vs X-ray | 1.62 | 2.06 | 1.27 | 1.82 |
| (SA)r vs X-ray | 1.64 | 2.14 | 1.28 | 1.87 |
| <SA> vs X-ray | 1.78 ± 0.12 | 2.37 ± 0.13 | 1.34 ± 0.10 | 2.04 ± 0.10 |

The NMR structures are denoted as follows: <SA> are the final 30 ensemble structures; SA is the mean structure obtaned from averaging the cartesian coordinates of individual ensemble members; and (SA)r is the minimized average structure obtained by regularization of SA. $E_{repel}$ was calculated using a final force constant of 4.0 kcal mol$^{-1}$ Å$^{-4}$ with van der Waals hard sphere radii scaled by 0.75. $E_{NOE}$ was calculated using a square-well potential with center-averaging and a force constant of 50 kcal mol$^{-1}$ Å$^{-2}$. $E_{cdih}$ was calculated using a force constant of 200 kcal mol$^{-1}$ rad$^{-2}$. $E_{bond}$, $E_{angle}$ and $E_{improper}$ were calculated using force constans of 1000 kcal mol$^{-1}$ Å$^{-2}$, 500 kcal mol$^{-1}$ rad$^{-2}$ and 500 kcal mol$^{-1}$ rad$^{-2}$, respectively.
[a]In all atomic rms differences calculations, only the backbone atoms (N, $C_\alpha$ and C) are included in the least squared best fitting. [b]Core helices A, B, C, and D.

TABLE 3

Interhelical and Kink Angles and Interhelical Distances for IL-6

| | Interhelical angles and distances[a] | | | |
|---|---|---|---|---|
| | Averaged, Minimized NMR | | X-Ray | |
| Helices | Angle | Distance | Angle | Distance |
| A:C | -151.3 | 8.6 | -152.7 | 9.2 |
| A:D | -153.4 | 8.5 | -154.5 | 9.1 |

TABLE 3-continued

Interhelical and Kink Angles and Interhelical Distances for IL-6

| B:C | −154.0 | 8.7  | −158.2 | 8.9  |
| --- | ------ | ---- | ------ | ---- |
| B:D | −142.1 | 9.2  | −149.1 | 9.6  |
| A:B | 44.9   | 12.5 | 40.2   | 13.4 |
| C:D | 40.2   | 13.1 | 35.0   | 13.5 |
| E:B | −53.3  | 10.8 | −49.5  | 9.6  |
| E:D | −176.2 | 9.0  | −170.6 | 8.9  |

Intrahelical Kink Angles

| Helix | Averaged, Minimized NMR | X-Ray |
| --- | --- | --- |
| A | 36.9 | ND |
| B | 23.6 | 30.8 |
| C | ND | ND |
| D | 17.2 | ND |

The algarithm of Chothia et al (Chothia et al, 1981) as implemented in CHARMM (Brooks et al, 1983) was used for the analysis.

TABLE 4

Residues Absolutely Conserved Among Nine Species of IL-6 (Residues 20–185)

| Residue | Location | Putative Role[b] |
| --- | --- | --- |
| I30 | helix A | bundle core packing |
| I37 | helix A | bundle core packing |
| E43 | helix A | none |
| C45 | helix A | disulfide bonding |
| C51 | AB loop | disulfide bonding |
| L58 | AB loop | receptor site III |
| E60 | AB loop | receptor site III |
| N61 | AB loop | receptor site III |
| L63 | AB loop | loop to helix D/E packing |
| L65 | AB loop | loop to helix B/E packing |
| P66 | AB loop | |
| D72 | AB loop | |
| C74 | AB loop | disulfide bonding |
| Q76 | AB loop | receptor site I |
| N80 | AB loop | |
| C84 | helix B | disulfide bonding |
| L85 | helix B | bundle core packing |
| G91 | helix B | bundle core packing |
| L92 | helix B | bundle core packing |
| E94 | helix B | |
| L99 | helix B | bundle core packing |
| L123 | helix C | bundle core packing |
| P142 | helix E | |
| L148 | helix E | side chain packing to helix B |
| W158 | helix D | receptor site III |
| L168 | helix D | bundle core packing |
| F174 | helix D | bundle core packing |
| L175 | helix D | bundle core packing |
| L179 | helix D | bundle core packing |
| R180 | helix D | receptor site I |
| R183 | helix D | receptor site I |

[b]putative roles for each residue were assigned on the following basis. Residues assigned to "bundle core packing" were found to be involved in the interior helical packing of the 4-helix bundle in Xu et al. (1996). Residues were assigned to specific receptor binding sites on the basis of published mutagenesis data or as defined in the legend to FIG. 7. Specific side chain packing to helices is based either on the results of XU et al. (1996) or the work presented here.

TABLE 5

Summary of Mutagenesis Data Defining Receptor Binding Sites on Select Cytokines[a]

| Cytokine | Site I Specificity Conferring | Site II Accessory-Signal Transduction | Site III Accessory-Signal Transduction |
| --- | --- | --- | --- |
| IL-6[b] | to IL-6Rα | to gp130 | to gp130 |
| | Q175, S176, S177, L178, R179, A180, L181, R182 | Y31, G35, S118, V121 | K46, S47, M49, E51, K54, W157, D160, T162 |
| CNTF[c] | to CNTF-Rα | to gp130 | to LIF-R |
| | R25, R28, Q63, W64, R171, R177 | K26, D30 | F152, K154, W157, G158, E153, K155 |
| LIF[d] | to LIF-R | to gp130 | to LIF-R |
| | K170, A174, V175 | Q25, S28, Q32, D120, I121, G124, S127 | P51, D57, P105, T150, K153, D154, A155, F156, K158, K159, K102 |
| | Accessory-Signal Transduction | Specificity Conferring | Specificity Conferring |

TABLE 5-continued

Summary of Mutagenesis Data Defining Receptor Binding Sites on Select Cytokines[a]

| IL-4[e] | to IL-2Rγ | to IL-4R | to IL-4R |
|---|---|---|---|
| | I11, R121, Y124, S125 | E9, S16, Q78, R81, R85 R88 | L109, N111, F112, L116 | a:: The three sites were defined topologically as: site I, c-terminus of D helix, n-terminus of A helix, plus portions of the AB loop; site II, on the A–C helical face; and site III, c-terminus of the A helix, n-terminus of the D helix, and portions of the AB and CD loops. Mutagenesis data was tabulated from the cited references and associated with one of the three sites. The functional consequence of each mutation was noted from the cited reference. Residues which roughly correspond to the geometric center of all mapped residues for that site are shown in bold.
b:: Mutagenesis data taken from Ciapponi et al., 1995; Savino et al., 1995a,b; Poanessa et al., 1995; Ehlers et al., 1994; Brakenhoff et al., 1994; De Hon et al., 1994.
c:: Mutagenesis data taken from Panayotatos et al., 1995; Thier et al., 1995; Inoue et al., 1995
d:: Mutagenesis data taken from Hudson et al., 1996; Layton et al., 1994.
e:: Mutagenesis data taken from Morrison and Leder, 1992; Kruse et al., 1993; Muller et al., 1994; Gustchina et al., 1995.

References

C. C. P. N. 4 (1994) *Acta Cyst*, D50, 760–767.

R. Arcone, P. Pucci, F. Zappacosta, V. Fontaine, A. Malorni, G. Marino and G. Ciliberto (1991) *Eur. J Biochem*., 198, 541–547.

L. S. Argetsinger, G. S. Cambell, X. Yang, B. A. Witthuhn, O. Silvennoinen, J. N. Ihle and C. Carter-Su (1993) *Cell*, 74,237–244.

J. F. Bazan (1990) *Immunology Today*, 11, 350–354.

J. F. Bazan (1991) *Neuron*, 7, 197–208.

J. P. J. Brakenhoff, F. D. de Hon, V. Fontaine, E. ten Boekel, H. Schooltink, S. Rose-John, P. C. Heinrich, J. Content and L. A. Aarden (1994) *The Journal of Biological Chemisty*, 269, 86–93.

A. T. Brunger (1992) *Nature*, 39, 472–474.

A. T. Brunger, J. Kuriyan and M. Karplus (1987) *Science*, 235, 458–460.

T. Clackson and J. A. Wells (1995) *Science*, 267, 383–386.

B. C. Cunningham and J. A. Wells (1989) *Science*, 244, 1081–1085.

S. Davis, T. H. Aldrich, D. M. Valenzuela, V. Wong, M. E. Furth, S. P. Squinto and G. D. Yancopoulos (1991) *Science*, 253, 59–63.

F. D. de Hon, E. ten Boekel, J. Herman, C. Clement, M. Ehlers, T. Taga, K. Yasukawa, Y. Ohsugi, T. Kishimoto, S. Rose-John, J. Wijdenes, R. Kastelein, L. A. Aarden and J. P. J. Brakenhoff (1995) *Cytokine*, 7, 398–407.

A. M. De Vos, M. Ultsch and A. A. Kossiakoff (1992) *Science*, 255, 306–312.

M. Ehlers, F. D. de Hon, H. K. Bos, U. Horsten, G. Kurapkat, H. S. van De Leur, J. Grotzinger, A. Wolimer, J. P. Brakenhoff and S. Rose-John (1995) *The Journal of Biological Chemistry*, 270, 8158–8163.

M. Ehlers, J. Grotzinger, F. D. deHon, J. Mullberg, J. P. J. Brakenhoff, J. Liu, A. Wollmer and S. Rose-John (1994) *Journal of Immunology*, 153, 1744–1753.

M. T. Fiorillo, A. Cabibbo, P. Iacopetti, E. Fattori and G. Ciliberto (1992) *Eur. J Immunol*., 22, 2609–2615.

V. Fontaine, R. Savino, R. Arcone, L. De Wit, J. P. J. Brackenhoff, J. Content and G. Ciliberto (1993) *European Journal of Biochemistry*, 211, 749–755.

D. P. Gearing, C. J. Thut, T. VandenBos, S. D. Gimpel, P. B. Delaney, J. King, V. Price, D. Cosman and M. P. Beckmann (1991) *EMBO Journal*, 10, 2839–2848.

G. Girasole, R. L. Jilka, G. Passeri, S. Boswell, G. Boder, D. C. Williams and S. C. Manolagas (1992) *The Journal of Clinical Investigations*, 89, 883–891.

A. Hammacher, L. D. Ward, J. Weinstock, H. Treutlein, K. Yasukawa and R. J. Simpson (1994) *Protein Science*, 3, 2280–2293.

W. A. Hendrickson (1985) *Methods in Enzymology*, 115, 252–270.

C. P. Hill, T. D. Osslund and D. Eisenberg (1993) *Proceedings of the National Acadademy of Sciences USA*, 90, 5167–5171.

T. Hirano, K. Yasukawa, H. Harada, T. Taga, Y. Watanabe, T. Matsuda, S. Kashiwamura, K. Nakajima, K. Koyama, A. Iwamatsu, S. Tsunasawa, F. Sakiyama, H. Matsui, Y. Takahara, T. Taniguchi and T. Kishimoto (1986) *Nature, 324, 73.*

R. L. Jilka, G. Hangoc, G. Girasole, G. Passeri, D. C. Williams, J. S. Abrams, B. Boyce, H. Broxmeyer and S. C. Manolagas (1992) *Science*, 257, 88–91.

T. A. Jones, J. Y. Zou, S. W. Cowan and M. Kjeldgaard (1991) *Acta Cryst*, A47, 110–119.

T. Kishimoto, S. Akira and T. Taga (1992) *Science*, 258, 593–597.

T. Kishimoto, T. Taga and S. Akira (1994) *Cell*, 76, 1–20.

R. A. Laskowski, M. W. MacArthur, D. S. Moss and J. M. Thornton (1993) *Journal of Applied Crystallography*, 26, 283–291.

B. Lovejoy, D. Cascio and D. Eisenberg (1993) *Jounal of Molecular Biology* (England), 234, 640–653.

C. Lutticken, A. Kruttgen, C. Moller, P. C. Heinrich and S. Rose-John (1991) *FEBS Lett*., 282, 265–267.

A. H. Mackiewicz, P. C. Schooltink, P. C. Heinrich and S. Rose-John (1992) *Journal of Immunology*, 149, 2021–2027.

A. Miyajima, T. Kitamura, N. Harada, T. Yokota and K. Arai (1992) *Annual Reviews in Immunology*, 10, 295–331.

M. Murakarni, M. Hibi, N. Nakagawa, T. Nakagawa, K. Yasukawa, K. Yamanishi, T. Taga and T. Kishimoto (1993) *Science*, 260, 1808–1810.

M. Murakami, M. Narazaki, M. Hibi, H. Yawata, K. Yasukawa, M. Hamaguchi, T. Taga and T. Kishimoto (1991) *Proc. Natl. Acad. Sci. USA*, 88, 11349–11353.

Z. Otwinowski (1991) In W. Wolf, P. R. Evans and A. G. W. Leslie (eds.), *Maximum likelihood refinement of heavy atom parameters*, pp. 23–38.

Z. Otwinowski (1993) In L. Sawyer, N. Isaacs and S. Bailey (eds.), Oscillation data reduction program.

G. Paonessa, R. Graziani, A. De Serio, R. Savino, L. Ciapponi, A. Lahm, A. L. Salvati, C. Toniatti and G. Ciliberto (1995) *The EMBO Journal*, 14, 1942–1951.

R. J. Reed (1986) *Acta Cryst*, A42, 140–149.

R. Savino, L. Ciapponi, A. Lahm, A. Demartis, A. Cabibbo, C. Toniatti, P. Delmastro, S. Altamura and G. Ciliberto (1994a) *EMBO J (England)*, 13, 5863–5870.

R. Savino, A. Lahm, M. Giorgio, A. Cabibbo, A. Tramontano and G. Ciliberto (1993). *Proceedings National Academy Science USA*, 90, 4067–4071.

R. Savino, A. Lahm; A. L. Salvati, L. Ciapponi, E. Sporeno, S. Altamura, G. Paonessa, C. Toniatti and G. Ciliberto (1994b) *The EMBO Journal*, 13, 1357–1367.

W. Somers, M. Ultsch, A. M. De Vos and A. A. Kossiakoff (1994) *Nature*, 372, 478–481.

S. R. Sprang and J. F. Bazan (1993) *Current Opinion in Structural Biology*, 3, 815–827.

T. Taga, M. Hibi, Y. Hirata, K. Yamasaki, K. Yasukawa, T. Matsuda, T. Hirano and T. Kishimoto (1989) *Cell*, 58, 573–581.

T. Taga, M. Narazaki, K. Yasukawa, T. Saito, D. Miki, M. Hamaguchi, S. Davis, M. Shoyab, G. D. Yancopoulos and T. Kishimoto (1992) *Prceedings of the National Acadamy of Science USA*, 89, 10998–11001.

B. C. Wang (1985) *Methods in Enzymology*, 115, 90–112.

L. D. Ward, G. J. Howlett, G. Discolo, K. Yasukawa, A. Hammacher, R. L. Moritz and R. J. Simpson (1994) *The Journal of Biological Chemistry*, 269, 23286–23289.

J. Wijdenes, P. C. Heinrich, G. Muller-Newen, C. Roche, Z. J. Gu, C. Clement and B. Klein (1995) *Eur. J. Immunol*, 25, 3474–3481.

G. G. Wong, J. S. Witek-Giannotti, P. A. Temple, R. Kriz, C. Ferenz, R. M. Hewick, S. C. Clark, K. Ikebuchi and M. Ogawa (1988) *The Journal of Immunology*, 140, 3040–3044.

K. Yamasaki, T. Taga, Y. Hirata, H. Yawata, Y. Kawanishi, B. Seed, T. Taniguchi, T. Hirano and T. Kishimoto (1988) *Science*, 241, 825–828.

H. Yawata, K. Yasukawa, S. Natsuka, M. Murakami, K. Yamasaki, M. Hibi, T. Taga and T. Kishimoto (1993) *The EMBO Journal*, 12, 1705–1712.

Bax, A., Max, D., & Zax, D. (1992) *J. Am. Chem. Soc.*, 114, 6924–6925.

Bax. A., Delaglio, F., Grzesiek, S., & Vuister, G., W. (1994) *J. Biomol. NMR.*, 4 787–797.

Bernard, A., Kopf, M., Kulbaki, R., Weich, N., Koehler, G., & Gutierrez-Ramos, J. C. (1994) *Immunity* 1, 725–731.

Brooks, B. R., Bruccoleri, R. E., Olafson, B. D., States, D. J., Swaminathan, S. & Karplus, M. (1983) *J. Comput. Chem.* 4, 187–217.

Brunger, A. T. (1993) X-PLOR Manual. Yale University, New Haven. Conn. Carson, M. (1991) *J. Appl. Cryst.* 24, 958–961.

Chothia, C., Levitt, M. & Richardson, D. (1981) *J. Mol. Biol.* 145, 215–250.

Clogston, C. L., Boone, T. C., Crandall, B. C., Mendiaz, E. A., & Lu, H. S. (1989) Arch.

*Biochem. Biophys.* 272, 144–151.

Clore, G. M. (1994) *J. Magn. Reson. Ser. B*, 104, 99–103.

Clore, G. M., Kay, L. E., Bax, A., and Gronenbom, A. M. (1991) *Biochemistry*, 30, 12–18.

Clubb, R. T., Tanabal, V., & Wagner, G. (1992) *J. Biomol. NMR* 2, 203–210.

Davis, S., Aldrich, T. H., Stahl, N., Pan, L., Taga, T., Kishimoto, T., Ip, N.Y., & Yancopoulos, G. D. (1993) *Science* 260, 1805–1808.

Feng, Y. Klein, B. K., and McWherter, C. A. (1996) *J. Mol. Biol.*, 259, 524–541.

Garrett, D. S., Powers, R., Gronenbom, A. M., & Clore, G. M. (1991) *J. Magn. Reson*, 95, 214–220.

Garratt, D. S., Kuszewski, J. Hancoca, T.J., Lodi, P. J., Vuister, G. W., Gronenborn, A. M. and Baldwin, E. T., Weber, I. T., St. Charles, R., Xuan, J. C., Appella, E., Yamada, M., Matsushima, K., Edwards, B. F. P., Clore, G. M., Gronenborn, A. M. and Alexander Wlodawer, A. (1991) *Proc. Natl. Acad. Sci. (USA)*, 88, 502–506.

Garrett, D. S., Powers, R., March, C. J., Frieden, E. A., Clore, G. M., & Gronenborn, A. M. (1992) *Biochemistry* 31, 4347–4353.

Grzesiek, S., Anglister, J., & Bax, A. (1993) *J. Magn. Reson.* 115, 114–119.

Grzesiek, S., & Bax, A. (1992a) *J. Magn. Reson.* 96, 432–440.

Grzesiek, S., & Bax, A. (1992b) *J. Am. Chem. Soc.* 114, 6291–6293.

Grzesiek, S., & Bax, A. (1993) *J. Am. Chem. Soc.* 115, 12593–12594.

Hirano, T., Yasukawa, K., Harada, H., Taga, T., Watanabe, Y., Matsuda, T., Kashiwamura, S., Nakajima, K., Koyama, K., Iwamatsu, A., Tsunasawa, S., Sakiyarna, F., Matsui, H., Takahara, Y., Taniguichi, T., & Kishimoto, T. (1986) *Nature* 324, 73–76.

Hirano, T., T., Akiro, S., Taga, T., & Kishimoto, T. (1990) *Immunol. Today* 11, 443–449.

Humphrey, W., Dalke, A., and Schulten, K. (1996) *J. Molec. Graphics* 14, 33–38.

Ikura, M., Bax, A., Clore, G. M., & Gronenborn, A. M (1990) *J. Am. Chem. Soc.* 112, 9020–9022.

Ishimi, Y., Miyaura, C., Jin, C. H., Akatsu, T., Abe, E., Nakamura, Y., Yamagurhi, A., Yoshiki, S., Matsuda, T., Hirano, T., & . . . (1990) *J. Immunol.* 145, 3297–3303.

Ivashkiv, L. B. (1995) *Immunity* 3, 1–14.

Kawano, M., Hirano, T., Matsuda, T., Taga, T., Horii, Y., Iwato, K., Asaoku, H., Tang, B., Tanabe, O., Tanaka, H., & Kishimoto, T. (1989) *Nature* 332, 93–85.

Kay, L. E., Ikura, M., Tschudin, R., & Bax, A. (1990a) *J. Magn. Reson.* 89, 496–514.

Kay, L. E., & Bax, A. (1990) *J. Magn. Reson.* 86, 110–126.

Kay, L. E., Keifer, P., & Saarinen, T. (1992a) *J. Am. Chem. Soc.* 114, 1063–1065.

Kay, L. E., Wittekind, M., McCoy, M. A., Friedrichs, M. S., & Mueller, L. (1992b) *J. Magn. Reson.* 98, 443–450.

Kay, L. E., Xu, G. Y., Singer, A. U., Muhandiram, D. R., & Forman-Kay, J. D. (1993a) *J. Magn. Reson. B*, 101, 333–337.

Kay, L. E. (1993) *J. Am. Chem. Soc.* 115 2055–2057.

Kay, L. E., (1995) *Prog. Biophys. Molec. Biol.*, 63, 277–299.

Kislbimoto, T. (1989) *Blood* 74, 1–10.

Kishimoto, T., Akira, S., & Taga, T. (1992) *Science* 258, 593–597.

Kruttgen, A., Rose-John, S., Moller, C., Wroblowski, B., Wollmer, A., Mullberg, J., Hirano, T., Kishimoto, T., & Heinrich, P. C. (1990) *FEBS Lett.* 262, 323–326.

Laskowski, R. A., MacArthur, W. M., Moss, D. S. and Thornton, J. M. (1993) *J. Appl. Cryst.*, 26, 283–291.

Li, X., Rock, F., Chong, P., Cockle, S., Keating, A., Ziltener, H., & Klein, M. *J. Bio. Chem.* 268, 22377–22384.

Marion, D., Kay, L. E., Sparks, S. W., Torchia, D. A., & Bax, A. (1989a) *J. Am. Chem. Soc.* 111, 1515–1517.

Marion, D., Driscoll, P. C., Kay, L. E., Wingfield, P. T., Bax, A., Gronenborn, A. M., & Clore, G. M. (1989b) *Biochemistry* 28, 6150–6156.

Marion, D., Ikura. M., Tschudin, R., & Bax, A. (1989c) *J. Magn. Reson.* 85, 393–399.

Marion, D., Ikura. M., & Bax, A. (1989d) *J. Magn. Reson.* 84, 425–430.

Mawatari, M., Kohno, K., Mizoguchi, H., Matsuda, T., Asoh, K., Van Damme, J., Welgus, H. G., & Kuwano, M. (1989) *J. Immunol.* 143, 1619–1627.

May, L. T., Santhanam, U., & Sehgal, P. B. (1991) *J. Biol. Chem.* 266, 9950–9955.

McDonald, N. Q., Panayotatos, N., & Hendrickson, W. A. (1995) *EMBO J.* 14, 2689–2699.

Messerle, B. A., Wider, G., Otting, G., Weber, C., & Wuthrich, K. (1989) *J. Magn. Reson.* 85,608–613.

Muhandiram. D. R., & Kay, L. E. (1994). *J. Magn. Reson. B* 103,203–216.

Murakami, M., Hibi, M., Nakagawa, N., Nakagawa, T., Yasukawa, K., Yamanishi, K., Taga, T., & Kishimoto, T. (1993) *Science* 260, 1808–1810.

Nilges, M., Clore, G. M. and Gronenborn, A. M. (1988) *FEBS Lett.* 229, 317–324.

Orita, T., Oh-eda, M., Hasegawa, M., Kuboniwa, H., Esaki, K., and Ochi, N. (1994) *J. Biochem. (Tokyo)* 115: 345–50.

Pandit, J., Bohm, A., Jancarik, J., Halenbeck, R., Koths, K., & Kim, S.-H. (1992) Science 258, 1358–1362.

Paonessa, G., Graziani, R., De Serio, A., Savino, R., Ciapponi, L., Lahm, A., Salvati, A. L., Toniatti, C., & Ciliberto, G. (1995) *EMBO J.* 14, 1942–1951.

Pascal, S. M., Muhandiram, D. R., Yamazaki, T., Forman-Kay, J. D., & Kay, L. E. (1994) *J. Magn. Reson. B*, 103, 197–201.

Powers, R., Garrett, D. S., March, C. J., Frieden, E. A., Gronenborn, A. M., & Clore, G. M. (1992) *Biochemistry* 31, 4334–4346.

Powers, R., Garrett, D. S., March, C. J., Frieden, E. A., Gronenborn, A. M., and Clore, G. M. (1993). *Biochemistry*, 32, 6744–6752.

Presnell, S. R., & Cohen, F. E. (1989) *Proc. Natl Acad. Sci USA* 86, 6592–6596.

Robinson, R. C., Grey, L. M., Staunton, D., Vankelecom, H., Vemallis, A. B., Moreau, J. F., Stuart, D. I., Heath, J. K., & Jones, E. Y. (1994) *Cell* 77, 1101–1116.

Sali, A., Potterton, L., Yuan, F., van Vlijmen, H., & Karplus, M. (1995) *Proteins: Struct. Func. Genet.* 23, 318–326.

Savino, R., Lahm, A., Giorgio, M., Cabibbo, A., Tramontano, A., & Cilberto, G. (1993) *Proc. Natl. Acad. Sci. USA* 90, 4067–4071.

Savino, R., Lahm, A., Salvati, Ciapponi, L., Sporeno, P., Altamura, A., Paonessa, G., Tonoatti, C., & Ciliberto, G. (1994) *EMBO J.* 13, 1357–1367.

Schleucher. J., Sattler, M., & Griesinger, C., (1993) *Angew. Chem., Int. Ed. Engl* 32, 1489–1491.

Spera, S., & Rax, A. (1991) *J. Am. Chem. Soc.* 113, 5490–5492.

Sprang, S. R., & Bazan, J. F. (1993) *Current Opin. Struct. Biol.* 3, 815–827.

Starnes, H. F., Pearce, M. K., Towari, A., Yim, J. H., Zou, J. C., & Abrams, J. S. (1990) *J. Immunol.* 145, 4185–4191.

Taga, T., Hirata, Y., Yamasali, K., Yasukawa, K., Matsuda, T., Hirano, T., & Kishimoto, T. (1989) *Cell* 58, 573–581.

Van Damme, J., Opdenakker, G., Simpson, R. J., Rubira, M. R., Cayphas, S., Vink, A., Billiau, A., & Van Snick, J. (1987) *J. Exp. Med.* 165, 914–919.

Vuister, G. W. & Bax, A. (1993). *J. Am. Chem. Soc.* 115, 7772–7777.

Vuister, G. W., Clore, G. M., Gronenborn, A. M., Powers, R., Garrett, D. S., Tschudin, R., and Bax, A. (1993) *J. Magn. Reson. Ser. B.*, 101, 210–213.

Ward, L. D., Hancher, A., Zhang, J. G., Weinstock, J., Yasukawa, K., Morton, C. J., Norton, R. S., & Simpson, R. J. *Protein Science* 2, 1472–1481.

Wittekind, M., & Mueller, L. (1993) *J. Magn. Reson. B* 101, 201–205.

Wuthrich, K. (1986) *NMR of proteins and Nucleic Acids*, John Wiley, New York. Xu, G. Y., Ong, E., Gilkes, N. R., Kilburn, D. G., Muhandiram, D. R., Harris-Brandts, M., Carver, J. P., Kay, L. E., and Harvey, T. S. (1995). *Biochemistry*, 34, 6993–7009.

Zhu, G. and Bax, A. (1992) *J. Magn. Reson.*, 100, 202–207.

Zuiderweg, E. R. P., Petros, A. M., Fesik, S. W., and Olejniczak, E. T. (1991) *J. Am. Chem. Soc.*, 113, 370–371.

All patent and literature references cited herein are incorporated by reference as if fully set forth.

What is claimed is:

1. A composition of matter comprising crystalline human interleukin-6 ("IL-6") in an effective carrier having diffracting crystals of a space group selected from the group consisting of P3121 and P3221.

2. The composition of matter of claim 1 wherein said IL-6 is recombinant IL-6.

3. The composition of matter of claim 1 wherein said IL-6 is glycosylated.

4. The composition of matter of claim 1 wherein said IL-6 comprises the mature sequence of naturally-occurring IL-6.

5. The composition of matter of claim 1 wherein said IL-6 comprises an additional N-terminal methionine residue.

6. The composition of matter of claim 1 wherein said crystals diffract to at least 1.9 Å resolution.

7. A composition of matter comprising IL-6 in crystalline association with a second chemical species in an effective carrier, wherein said second chemical species is selected from the group consisting of an antagonist of IL-6 activity, an agonist of IL-6 activity, and all or a portion of an IL-6 receptor ("IL-6R").

8. Crystalline human interleukin-6 ("IL-6") having diffracting crystals of a space group selected from the group consisting of P3121 and P3221.

9. The crystalline IL-6 of claim 8 wherein said IL-6 is recombinant IL-6.

10. The crystalline IL-6 of claim 8 wherein said IL-6 is glycosylated.

11. The crystalline IL-6 of claim 8 wherein said IL-6 comprises the mature sequence of naturally-occurring IL-6.

12. The crystalline IL-6 of claim 8 wherein said IL-6 comprises an additional N-terminal methionine residue.

13. The crystalline IL-6 of claim 8 wherein said crystals diffract to at least 1.9 Å resolution.

14. A crystalline composition comprising IL-6 in association with a second chemical species in an effective carrier, wherein said second chemical species is selected from the group consisting of an antagonist of IL-6 activity and an agonist of IL-6 activity.

* * * * *